United States Patent
Sasai et al.

(10) Patent No.: US 10,781,420 B2
(45) Date of Patent: Sep. 22, 2020

(54) METHOD FOR PRODUCING CEREBELLAR PROGENITOR TISSUE

(71) Applicants: RIKEN, Wako-shi, Saitama (JP); SUMITOMO CHEMICAL COMPANY, LIMITED, Tokyo (JP)

(72) Inventors: Yoshiki Sasai, Wako (JP); Keiko Muguruma, Wako (JP)

(73) Assignees: RIKEN, Wako (JP); SUMITOMO CHEMICAL COMPANY, LIMITED, Tokyo (JP)

( * ) Notice: Subject to any disclaimer, the term of this patent is extended or adjusted under 35 U.S.C. 154(b) by 0 days.

(21) Appl. No.: 15/509,387

(22) PCT Filed: Sep. 8, 2015

(86) PCT No.: PCT/JP2015/075412
§ 371 (c)(1),
(2) Date: Mar. 7, 2017

(87) PCT Pub. No.: WO2016/039317
PCT Pub. Date: Mar. 17, 2016

(65) Prior Publication Data
US 2017/0253853 A1    Sep. 7, 2017

(30) Foreign Application Priority Data
Sep. 8, 2014 (JP) .................... 2014-182758

(51) Int. Cl.
| | | |
|---|---|---|
| *C12N 5/0793* | (2010.01) | |
| *C12N 5/10* | (2006.01) | |
| C12N 15/09 | (2006.01) | |

(52) U.S. Cl.
CPC ............. *C12N 5/0619* (2013.01); *C12N 5/10* (2013.01); *C12N 15/09* (2013.01); *C12N 2500/90* (2013.01); *C12N 2501/113* (2013.01); *C12N 2501/19* (2013.01); *C12N 2501/21* (2013.01); *C12N 2501/33* (2013.01); *C12N 2506/03* (2013.01); *C12N 2506/08* (2013.01)

(58) Field of Classification Search
CPC .............. C12N 5/0619; C12N 2506/08; C12N 2501/19; C07K 14/435; C07K 14/495; C07K 14/50
See application file for complete search history.

(56) References Cited

U.S. PATENT DOCUMENTS

2010/0009442 A1    1/2010    Sasai et al.

FOREIGN PATENT DOCUMENTS

| EP | 1783205 A1 | 5/2007 |
|---|---|---|
| JP | 2008-099662 A | 5/2008 |
| JP | 2014-023457 A | 2/2014 |
| WO | WO 2008/035110 A | 5/2008 |

OTHER PUBLICATIONS

Su et al., Dev Biol., 290:287-296, 2006.*
Liu et al. Annu Rev Neurosci., 24:869-896, 2001.*
Tiveron et al., Curr Opin Neurobio, 18:237-244, 2008.*
Chizhikov et al., Development, 133:2793-2804, 2006.*
Ben-Arie et al., "Math1 is essential for genesis of cerebellar granule neurons," *Nature*, 390(6656): 169-172 (1997).
Carletti et al., "Neurogenesis in the Cerebellum," *Neuroscientist*, 14(1): 91-100 (2008).
Erceg et al., "Efficient Differentiation of Human Embryonic Stem Cells into Functional Cerebellar-Like Cells," *Stem Cells Dev.*, 19(11): 1745-1756 (2010).
Fink et al., "Development of the Deep Cerebellar Nuclei: Transcription Factors and Cell Migration from the Rhombic Lip," *J. Neurosci.*, 26(11): 3066-3076 (2006).
Fischer et al., "Fgf15-mediated control of neurogenic and proneural gene expression regulates dorsal midbrain neurogenesis," *Dev. Biol.*, 350(2): 496-510 (2011).
Gimeno et al., "Expression of Chick Fgf19 and Mouse Fgf15 Orthologs is Regulated in the Developing Brain by Fgf8 and Shh," *Dev. Dyn.*, 236(8): 2285-2297 (2007).
Hoshino et al., "Ptf1a, a bHLH Transcriptional Gene, Defines GABAergic Neuronal Fates in Cerebellum," *Neuron*, 47(2): 201-213 (2005).
Joyner et al., "Otx2, Gbx2, and Fgf8 interact to position and maintain a mid-hindbrain organizer," *Curr. Opin. Cell Biol.*, 12(6): 736-741 (2000).
Ma et al., "Impaired B-lymphopoiesis, myelopoiesis, and derailed cerebellar neuron migration in CXCR4- and SDF-1-deficient mice," *Proc. Natl. Acad. Sci. USA*, 95(16): 9448-9453 (1998).
Machold et al., "Math1 Is Expressed in Temporally Discrete Pools of Cerebellar Rhombic-Lip Neural Progenitors," *Neuron*, 48(1): 17-24 (2005).
Reiss et al., "Stromal Cell-Derived Factor 1 is Secreted by Meningeal Cells and Acts as Chemotactic Factor on Neuronal Stem Cells of the Cerebellar External Granular Layer," *Neuroscience*, 115(1): 295-305 (2002).

(Continued)

*Primary Examiner* — Kimberly Ballard
*Assistant Examiner* — Stacey N MacFarlane
(74) *Attorney, Agent, or Firm* — Leydig, Voit & Mayer, Ltd.

(57) ABSTRACT

The present invention provides a method for producing a human cell aggregate containing a midbrain-hindbrain boundary neural progenitor tissue, including subjecting an aggregate of human pluripotent stem cells to suspension culturing in a serum-free medium containing insulin, and treating, in the suspension culturing, the aggregate of human pluripotent stem cells or a human cell aggregate derived therefrom with a ROCK inhibitor, a TGFβ signal inhibitor, and a first fibroblast growth factor. Furthermore, the human cell aggregate containing the midbrain-hindbrain boundary neural progenitor tissue is subjected to suspension culturing in a serum-free medium to induce formation of a neuroepithelial structure by neural progenitor in the neural progenitor tissue, whereby the human cell aggregate containing the cerebellar plate tissue can be obtained.

12 Claims, 9 Drawing Sheets

(56) References Cited

OTHER PUBLICATIONS

Tao et al., "Efficient Generation of Mature Cerebellar Purkinje Cells From Mouse Embryonic Stem Cells," *J. Neurosci, Res*, 88(2): 234-247 (2010).

Wang et al., "Math1 Expression Redefines the Rhombic Lip Derivatives and Reveals Novel Lineages within the Brainstem and Cerebellum," *Neuron*, 48(1): 31-43 (2005).

Wingate et al., "The role of the rhombic lip in avian cerebellum development," *Development*, 126(20): 4395-4404 (1999).

Zervas et al., "Cell Behaviors and Genetic Lineages of the Mesencephalon and Rhombomere 1," *Neuron*, 43(3): 345-357 (2004).

Zhu et al., "Role of the chemokine SDF-1 as the meningeal attractant for embryonic cerebellar neurons," *Nat. Neurosci.*, 5(8): 719-720 (2002).

Zou et al., "Function of the chemokine receptor CXCR4 in haematopoiesis and in cerebellar development," *Nature*, 393(6685): 595-599 (1998).

Chambers et al., "Highly efficient neural conversion of human ES and iPS cells by dual inhibition of SMAD signaling," *Nat. Biotechnol.*, 27(3): 275-280 (2009).

Cheng et al., "Widespread Contribution of Gdf7 Lineage to Cerebellar Cell Types and Implications for Hedgehog-Driven Medulloblastoma Formation," *PLoS One*, 7(4): e35541 (2012).

Muguruma et al., "Ontogeny-recapitulating generation and tissue integration of ES cell-derived Purkinje cells," *Nat. Neurosci.*, 13(10): 1171-1180 and Supplementary Figures and Table (2010).

Muguruma et al., "In vitro recapitulation of neural development using embryonic stem cells: From neurogenesis to histogenesis," *Dev. Growth Differ.*, 54(3): 349-357 (2012).

Muguruma et al., "Self-Organization of Polarized Cerebellar Tissue in 3D Culture of Human Pluripotent Stem Cells," *Cell Rep.*, 10(4): 537-550 (2015).

Nakano et al., "Self-Formation of Optic Cups and Storable Stratified Neural Retina from Human ESCs," *Cell Stem Cell*, 10(6): 771-785 and Supplemental Information (2012).

Ten Donkelaar et al., "Development of the Human Cerebellum and Its Disorders," *Clin. Perinatol.*, 36: 513-530 (2009).

Watanabe et al., "A ROCK inhibitor permits survival of dissociated human embryonic stem cells," *Nat. Biotechnol.*, 25(6): 681-686 (2007).

Wataya et al., "Minimization of exogenous signals in ES cell culture induces rostral hypothalamic differentiation," *Proc. Natl. Acad. Sci. USA*, 105(33): 11796-11801 (2008).

Zhu et al., "SDF1/CXCR4 signalling regulates two distinct processes of precerebellar neuronal migration and its depletion leads to abnormal pontine nuclei formation," *Development*, 136(11): 1919-1928 (2009).

Intellectual Property Office of Singapore, Written Opinion in Singaporean Patent Application No. 11201701857Q (dated Dec. 12, 2017).

Japanese Patent Office, International Search Report in International Patent Application No. PCT/JP2015/075412 (dated Dec. 15, 2015).

Japanese Patent Office, Written Opinion of the International Searching Authority in International Patent Application No. PCT/JP2015/075412 (dated Dec. 15, 2015).

Luo et al., "Functional SDF1α/CXCR4 signaling in the developing spinal cord," *J. Neurochem.*, 93(2): 452-462 (2005).

Miyake et al., "Fgf19 regulated by Hh signaling is required for zebrafish forebrain development," *Dev. Biol.*, 288(1): 259-275 (2005).

Su et al., "Generation of cerebellar neuron precursors from embryonic stem cells," *Dev. Biol.*, 290(2): 287-296 (2006).

European Patent Office, Supplementary European Search Report in European Patent Application No. 15840073 (dated Apr. 23, 2018).

European Patent Office, Supplementary European Search Report in European Patent Application No. 18168060 (dated May 15, 2018).

Barkho et al., "Endogenous Matrix Metalloproteinase (MMP)-3 and MMP-9 Promote the Differentiation and Migration of Adult Neural Progenitor Cells in Response to Chemokines," *Stem Cells*, 26(12): 3139-3149 (2008).

Smith et al., "Inhibition of Activin/Nodal signaling promotes specification of human embryonic stem cells into neuroectoderm," *Dev. Biol.*, 313(1): 107-117 (2008).

European Patent Office, Communication Pursuant to Article 94(3) EPC in European Patent Application No. 18168060.4 (dated Oct. 9, 2019).

\* cited by examiner

METHOD FOR PRODUCING CEREBELLAR PROGENITOR TISSUE

CROSS-REFERENCE TO RELATED APPLICATIONS

This patent application is the U.S. national phase of International Patent Application No. PCT/JP2015/075412, filed on Sep. 8, 2015, which claims the benefit of Japanese Patent Application No. 2014-182758, filed on Sep. 8, 2014, the disclosures of which are incorporated herein by reference in their entireties for all purposes.

TECHNICAL FIELD

The present invention relates to a technique for inducing differentiation of human pluripotent stem cells into cerebellar progenitor tissue in vitro.

BACKGROUND ART

The cerebellum, a major component of the motor system, is a highly ordered brain structure with several well-defined types of cells. The early development of the cerebellum is conserved among amniotes including human. The initial phase of cerebellar development is the formation of the isthmic organizer, which lies at the midbrain-hindbrain boundary (MHB). Under its inductive influence, the cerebellar anlage arises in the dorsal region (alar plate) of rhombomere 1 (r1) (non-patent documents 1-3). Cerebellar cells are generated in two distinct germinal zones in r1. One is the ventricular zone (VZ) of the cerebellar plate, which expresses the basic helix-loop-helix (bHLH) transcription factor Ptf1a. The Ptf1a$^+$ progenitors produce GABAergic neurons of the cerebellar cortex (Purkinje cells and interneurons) and of the deep cerebellar nuclei (DCN). The other zone is the rhombic lip (RL), which expresses another bHLH factor, Atoh1 (also known as Math1). The Atoh1$^+$ progenitors generate cerebellar glutamatergic neurons, including granule cells (GC), unipolar brush cells, and large DCN projection neurons (non-patent documents 4-9). Much progress has been made over the decade in understanding the control of cellular differentiation of the cerebellum. Such knowledge has promoted technical advancement for in vitro generation of cerebellar neuronal components from pluripotent stem cells (non-patent documents 10-13). However, it remains largely elusive how the generated cellular components are assembled to form the intricate structure of the cerebellum.

The present inventors previously reported that cerebellar neurons could be efficiently generated from mouse embryonic stem cells (mESCs) by recapitulating the self-inductive signaling microenvironment in three-dimensional (3D) culturing (non-patent document 11). mESCs have the potential to form some isthmic organizer tissue within the aggregate in response to Fgf2 and Insulin. Under those conditions, mESC-derived neural progenitors differentiate into cerebellar plate NE that expresses the Purkinje cell-progenitor marker Kirrel2 (also known as Neph3), when endogenous Shh signaling is inhibited with an inhibitor. On the other hand, the addition of BMP signals to culture promoted differentiation into Atoh1$^+$ GCs and Tbr1$^+$ DCN neurons, while it suppressed the generation of Purkinje cells in the mESC aggregate. Although cerebellar neuron differentiation can be successfully induced in mESCs, 3D formation of cerebellar anlage structures has not been so far recapitulated.

It has been reported that Fgf19, a human ortholog of mouse Fgf15 (expressed in the MHB), is implicated in development of dorsal progenitors in the hindbrain (non-patent documents 14 and 15).

SDF1 (also known as CXCL12), a secreted ligand for chemokine receptor 4 (CXCR4), is expressed in meningeal cells and plays a crucial role in the migration of external granule (EGL) cells, which express CXCR4 (non-patent documents 16-19). SDF1- or CXCR4-deficient mice developed abnormally with an irregular external granular layer (EGL) and ectopically located Purkinje cells.

The present inventors have found that an inhibitor of Rho-associated coiled-coil kinase (ROCK) suppresses cell death of pluripotent stem cells (particularly, human pluripotent stem cells) induced by dispersion (patent documents 1 and 2).

DOCUMENT LIST

Patent Documents patent document 1: JP-A-2008-99662
patent document 2: WO 2008/035110

Non-Patent Documents non-patent document 1: Wingate, R. J. T, and Hatten, M. E. (1999). The role of the rhombic lip in avian cerebellum development. Development 126, 4395-4404.
non-patent document 2: Joyner, A. L., Liu, A., and Millet, S. (2000). Otx2, Gbx2 and Fgf8 interact to position and maintain a mid-hindbrain organizer. Curr. Opin. Cell Biolo. 12, 736-741.
non-patent document 3: Zervas, M., Milet, S., Ahn, S., and Joyner, A. L. (2004). Cell behavior and genetic lineage of the mesencephalon and rhombomere 1. Neuron 43, 345-357.
non-patent document 4: Ben-Arie, N., Bellen, H. J., Armstrong, D. L. McCall, A. E., Gordadze, P. R., Guo, Q., Matzuk, M. M., and Zoghbi, H. (1997). Math1 is essential for genesis of cerebellar granule neurons. Nature 390, 169-172.
non-patent document 5: Hoshino, M., Nakamura, S., Mori, K., Kawauchi, T., Terao, M., Nishimura, Y. V., Fukuda, A., Fuse, T., Matsuo, N., Sone, M., Watanabe, M., Bito, H., Terashima, T., Wright, C. V. E., Kawaguchi, Y., Nakano, K., and Nabeshima, Y. (2005). Ptf1a, a bHLH transcriptional gene, defines GABAergic neuronal fates in cerebellum. Neuron 47, 201-213.
non-patent document 6: Machold, R., and Fishell, G. (2005). Math1 is expressed in temporally discrete pools of cerebellar rhombic-lip neural progenitors. Neuron 48, 17-24.
non-patent document 7: Wang, V. Y., Rose, M. F., and Zoghbi, H. Y. (2005). Math1 expression redefines the rhombic lip derivatives and reveals novel lineages within the brainstem and cerebellum. Neuron 48, 31-43.
non-patent document 8: Fink, A. J., Englund, C., Daza, R. A. M., Pham, D., Lau, C., Nivison, M., Kowalczyk, T., and Hevner, R. F. (2006). Development of the deep cerebellar nuclei: Transcription factors and cell migration from the rhombic lip. J. Neurosci. 26, 3066-3076.
non-patent document 9: Carletti, B., and Rossi, F. (2008). Neurogenesis in the cerebellum. Neuroscientist 14, 91-100.
non-patent document 10: Su, H.-L., Muguruma, K., Matsuo-Takasaki, M., Kengaku, M., Watanabe, K., and Sasai, Y.

(2006). Generation of cerebellar neuron precursors from embryonic stem cells. Dev. Biol. 290, 287-296.
non-patent document 11: Muguruma, K., Nishiyama, A., Ono, Y., Miyawaki, H., Mizuhara, E., Hori, S., Kakizuka, A., Obata, K., Yanagawa, Y., Hirano, T., and Sasai, Y. (2010). Ontogeny-recapitulating generation and tissue integration of ES cell-derived Purkinje cells. Nature Neurosci. 13, 1171-1180.
non-patent document 12: Tao, O., Shimazaki, T., Okada, Y., Naka, H., Kohda, K., Yuzaki, M., Mizusawa, H., and Okano, H. (2010). Efficient generation of mature cerebellar Purkinje cells from mouse embryonic stem cells. J. Neurosci. Res. 88, 234-247.
non-patent document 13: Erceg, S., Ronaghi, M., Zipancic, I., Lainez, S., Rosello, M. G., Xiong, C., Moreno-Manzano, V., Rodriguez-Jimenez, F. J., Planells, R., Alvarez-Dolado, M., Bhattacharya, S. S., and Stojkovic, M. (2010). Efficient differentiation of human embryonic stem cells into functional cerebellar-like cells. Stem Cells Dev., 19, 1745-1756.
non-patent document 14: Gimeno, L., and Martinez, S. (2007) Expression of chick Fgf19 and mouse Fgf15 orthologs is regulated in the developing brain by Fgf8 and Shh. Dev. Dyn. 236, 2285-2297.
non-patent document 15: Fischer, T., Faus-Kessler, T., Welzl, G., Simeone, A., Wurst, W., and Prakash, N. (2011) Fgf15-mediated control of neurogenic and proneural gene expression regulates dorsal midbrain neurogenesis. Dev. Biol. 350, 496-510.
non-patent document 16: Ma, Q., Jones, D., Borghesani, P. R., Segal, R. A., Nagasawa, T., Kishimoto, T., Bronson, R. T., and Springer, T. A. (1998). Impaired B-lymphopoiesis, myelopoiesis, and derailed cerebellar neuron migration in CXCR4- and SDF-1-deficient mice. Proc. Natl. Acad. Sci. USA 95, 9448-9453.
non-patent document 17: Reiss, K., Mentlein, R., Sievers, J., and Hartmann, D. (2002). Stromal cell-derived factor 1 is secreted by meningeal cells and act as chemotactic factor on neuronal stem cells of the cerebellar external granular layer. Neurosci. 115, 295-305.
non-patent document 18: Zou, Y.-R., Kottmann, A. H. Kuroda, M., Taniuchi, I., and Littman, D. R. (1998). Function of the chemokine receptor CXCR4 in haematopoiesis and in cerebellar development. Nature 393, 595-599.
non-patent document 19: Zhu, Y., Yu, T., Zhang, X.-C., Nagasawa, T., Wu, J. Y., and Rao, Y. (2002). Role of the chemokine SDF-1 as the meningeal attractant for embryonic cerebellar neurons. Nature Neurosci. 5, 719-720.

SUMMARY OF THE INVENTION

Problems to be Solved by the Invention

As mentioned above, it has been reported that mouse pluripotent stem cells can differentiate into cerebellar progenitors when subjected to aggregate suspension culturing in a medium containing FGF2 and insulin (non-patent document 11). However, it was found that, when culturing conditions for mouse pluripotent stem cells are directly applied to human pluripotent stem cells, cerebellar differentiation of human pluripotent stem cells is not supported, and cerebellar differentiation is not observed and neural culturing itself cannot be continued due to collapse of aggregates and others. In addition, Hedgehog inhibitor (Cyclopamine) that greatly promoted induction of differentiation of mouse pluripotent stem cells into cerebellar progenitor tissue did not significantly promote cerebellar plate formation from human pluripotent stem cells. It was suggested that the conditions for differentiation of cerebellar progenitor tissue from human pluripotent stem cells are vastly distinct from those of mouse, since, for example, addition of Sonic Hedgehog to human pluripotent stem cell culturing system conversely promotes formation of polarized cerebellar plate.

Thus, the present invention aims to provide a technique for inducing cerebellar tissue or a progenitor tissue thereof in vitro from human pluripotent stem cells.

Means of Solving the Problems

The present inventors applied the self-formation principle to human ESC culturing for the generation of human cerebellar tissues in vitro. Using modified culturing conditions including addition of ROCK inhibitor (Y-27632) or TGF-beta inhibitor (SB431542) and omitting addition of Hedgehog inhibitor and others, they have enabled for the first time differentiation of cerebellar progenitor tissue from human pluripotent stem cells in vitro. Moreover, in the course of optimizing 3D culturing conditions, the present inventors identified two factors, Fgf19 and SDF1, which promote self-formation of ordered cerebellar plate-like tissues in distinct manners. Addition of Fgf19 to aggregate culturing promoted cerebellar plate formation from human pluripotent stem cells and enhanced dorsal-ventral (DV) polarity in the midbrain-hindbrain boundary neural tissue in the aggregate. Additional treatment of SDF1 in self-forming hESC culturing for cerebellar tissue induces the generation of continuous cerebellar-plate NE that are stratified as seen in the early cerebellar plate. Furthermore, neuroectoderm (NE) margins form distinct RL-like germinal zones consisting of Atoh1$^+$/Barh1$^+$ cells. In addition, addition of Gdf7 during the process of self organization of cerebellar progenitor tissue (cerebellar plate tissue) promoted formation of rhombic lip in the cerebellar plate tissue.

The present inventors have conducted further studies based on the above-mentioned findings and completed the present invention.

Therefore, the present invention is as follows:

[1] A method for producing a human cell aggregate comprising a cerebellar progenitor tissue, comprising subjecting an aggregate of human pluripotent stem cells to suspension culturing in a serum-free medium containing insulin, and treating, in the suspension culturing, the aggregate of human pluripotent stem cells or a human cell aggregate derived therefrom with a ROCK inhibitor, a TGFβ signal inhibitor, and a first fibroblast growth factor.

[2] The production method of [1], wherein the cerebellar progenitor tissue is a midbrain-hindbrain boundary neural progenitor tissue.

[3] The production method of [1] or [2], wherein the aggregate of human pluripotent stem cells or a human cell aggregate derived therefrom is not treated with BMP4 in the suspension culturing.

[4] The production method of any of [1] to [3], wherein the aggregate of human pluripotent stem cells or a human cell aggregate derived therefrom is not treated with a sonic hedgehog inhibitor in the suspension culturing.

[5] The production method of any of [1]-[4], wherein the first fibroblast growth factor is FGF2 or FGF8.

[6] The production method of [1], comprising
(I) subjecting an aggregate of human pluripotent stem cells to suspension culturing in a serum-free medium containing insulin, and treating, in the suspension culturing, the aggregate of human pluripotent stem cells or a human cell aggregate derived therefrom with a ROCK inhibitor, a TGFβ signal inhibitor, and a first fibroblast growth factor, to obtain a human cell aggregate containing a midbrain-hindbrain boundary neural progenitor tissue, and (II) subjecting the obtained human cell aggregate containing the midbrain-hindbrain boundary neural progenitor tissue to further suspension culturing in a serum-free medium to induce formation of a neuroepithelial structure by neural progenitors in the neural progenitor tissue, thereby obtaining the human cell aggregate containing the cerebellar plate tissue.

[7] The production method of [6], which comprises further treating, in the suspension culturing in step (I), the aggregate of human pluripotent stem cells or the human cell aggregate derived therefrom with a second fibroblast growth factor.

[8] The production method of [7], wherein the second fibroblast growth factor is FGF19, FGF17 or FGF8.

[9] The production method of any of [6]-[8], which comprises treating, in the suspension culturing in step (II), the human cell aggregate containing the midbrain-hindbrain boundary neural progenitors or a human cell aggregate derived therefrom with SDF1.

[10] The production method of [6], which comprises treating, in the suspension culturing in step (II), the human cell aggregate containing the midbrain-hindbrain boundary neural progenitors or a human cell aggregate derived therefrom with GDF7.

[11] The production method of [7] or [8], wherein the cerebellar plate tissue is a neuroepithelial structure comprising GABAergic neural progenitors and cerebellar granule cell progenitors.

[12] The production method of [11], wherein the neuroepithelial structure has dorsal-ventral polarity.

[13] The production method of [9], wherein the cerebellar plate tissue comprises continuous cerebellar neuroepithelial structure and rhombic lip-like tissue on a surface layer region of the cell aggregate.

[14] The production method of [13], wherein the cerebellar plate tissue has a three-layer structure which comprises ventricular zone, Purkinje cell zone and rhombic lip-derived cell zone, stratified in the order from the apical surface.

[15] A human cell aggregate obtained by the production method of any one of [1]-[14].

[16] A method for producing human Purkinje cells, human Golgi cells or human interneurons, comprising (I) obtaining a human cell aggregate containing cerebellar plate tissue from human pluripotent stem cells by the production method of any of [6]-[14], (II) obtaining a GABAergic neural progenitors from the obtained human cell aggregate, and (III) coculturing the GABAergic neural progenitors with mammalian cerebellar granule cell progenitors to induce differentiation of the GABAergic neural progenitors into Purkinje cells, Golgi cells or interneurons.

[17] A method for producing human cerebellar granule cells, comprising (I) obtaining a human cell aggregate containing cerebellar plate tissue from human pluripotent stem cells by the production method of any of [6]-[14], (II) obtaining cerebellar granule cell progenitors from the obtained human cell aggregate, and (III) coculturing the cerebellar granule cell progenitors with mammalian cerebellar cell to induce differentiation into cerebellar granule cells.

Effect of the Invention

According to the present invention, a cerebellar progenitor tissue can be efficiently induced in vitro from human pluripotent stem cells. A midbrain-hindbrain boundary progenitor tissue can be formed from human pluripotent stem cells for the first time in vitro. The dorsal-ventral polarity observed in vivo can be reproduced in this midbrain-hindbrain boundary progenitor tissue. According to the present invention, a cerebellar progenitor tissue (cerebellar plate tissue) having a continuous epithelial structure can be self-organized in an aggregate of human pluripotent stem cell-derived cells. In this human cerebellar plate tissue, cerebellar neuroepithelium (a progenitor tissue of cerebellar Purkinje cells and interneurons) and rhombic lip (progenitor tissue of cerebellar granule cell and cerebellar nuclei nerve cell), which are two major regions observed in vivo, may be adjacently self-formed. In addition, differentiation of the in vitro-induced human cerebellar plate tissue into Purkinje cells, cerebellum interneurons, cerebellar granule cells, cerebellar nuclei and others can be further induced.

Figure 1:
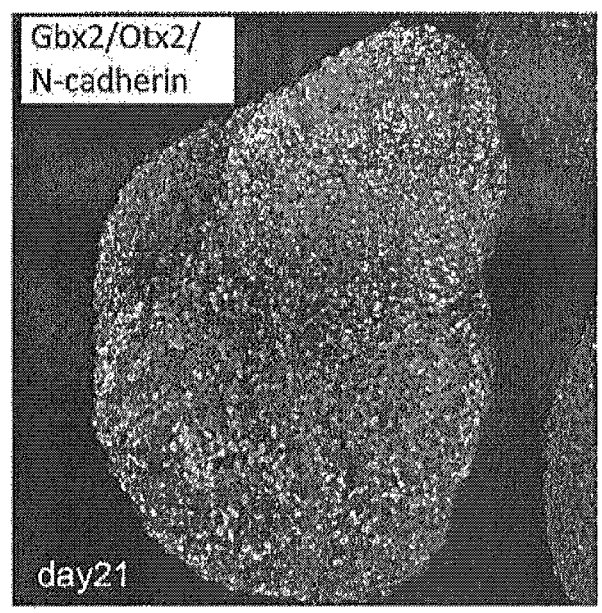
FIG. 1 shows a fluorescent immunohistochemical staining image of a cell aggregate using antibodies against Gbx2 (green), Otx2 (red) and N-cadherin (blue).

DESCRIPTION OF EMBODIMENTS (1) Pluripotent Stem Cell

The "pluripotent stem cell" refers to a cell having both the potential for differentiating into all cells constituting the body (pluripotency), and the potential for producing daughter cells having the same differentiation potency via cell division (self-replication competence).

The pluripotency can be evaluated by transplanting the cells of an evaluation target into a nude mouse, and testing the presence or absence of formation of teratoma containing each cell of three germ layers (ectoderm, mesoderm, endoderm).

Examples of the pluripotent stem cell include embryonic stem cell (ES cell), embryonic germ cell (EG cell), induced pluripotent stem cell (iPS cell) and others, and the pluripotent stem cell is not limited as long as it has both the pluripotency and the self-replication competence. In the present invention, embryonic stem cells or induced pluripotent stem cells are preferably used.

Embryonic stem cells (ES cells) can be established by culturing, for example, a pre-implantation early embryo, an inner cell mass that constitutes the early embryo, a single blastomere and others (Manipulating the Mouse Embryo A Laboratory Manual, Second Edition, Cold Spring Harbor Laboratory Press (1994); Thomson, J. A. et al., Science, 282, 1145-1147 (1998)). As the early embryo, an early embryo prepared by nuclear-transplanting the nucleus of a somatic cell may be used (Wilmut et al. (Nature, 385, 810 (1997)), Cibelli et al. (Science, 280, 1256 (1998)), Akira IRITANI et al. (Tanpakushitsu Kakusan Koso, 44, 892 (1999)), Baguisi et al. (Nature Biotechnology, 17, 456 (1999)), Wakayama et al. (Nature, 394, 369 (1998); Nature Genetics, 22, 127 (1999); Proc. Natl. Acad. Sci. USA, 96, 14984 (1999)), Rideout III et al. (Nature Genetics, 24, 109 (2000), Tachibana et al. (Human Embryonic Stem Cells Derived by Somatic Cell Nuclear Transfer, Cell (2013) in press)). As an early embryo, a parthenogenetic embryo may also be used (Kim et al. (Science, 315, 482-486 (2007)), Nakajima et al. (Stem Cells, 25, 983-985 (2007)), Kim et al. (Cell Stem Cell, 1, 346-352 (2007)), Revazova et al. (Cloning Stem Cells, 9, 432-449 (2007)), Revazova et al. (Cloning Stem Cells, 10, 11-24 (2008)).

Fusion ES cell obtained by cell fusion of ES cell and somatic cell is also included in the embryonic stem cells used for the method of the present invention.

Embryonic stem cells are available from appropriate organizations, and commercial products may be purchased. For example, the human embryonic stem cells KhES-1, KhES-2 and KhES-3 are available from the Institute for Frontier Medical Sciences, Kyoto University.

Embryonic germ cells (EG cells) can be established by culturing primordial germ cells in the presence of LIF, bFGF and SCF (Matsui et al., Cell, 70, 841-847 (1992), Shamblott et al., Proc. Natl. Acad. Sci. USA, 95(23), 13726-13731 (1998), Turnpenny et al., Stem Cells, 21(5), 598-609, (2003)).

Induced pluripotent stem cell (iPS cell) refers to a cell that artificially acquired pluripotency and self-replication competence by bringing a somatic cell (e.g., fibroblast, skin cell, lymphocyte etc.) into contact with nuclear reprogramming factors. iPS cell was found for the first time by a method including introduction of nuclear reprogramming factors composed of Oct3/4, Sox2, Klf4 and c-Myc into somatic cells (e.g., fibroblast, skin cell etc.) (Cell, 126: p. 663-676, 2006). Thereafter, many researchers have made various improvements in the combination of reprogramming factors and introduction method of the factors, and various production methods of induced pluripotent stem cell have been reported.

The nuclear reprogramming factors may be configured with any substance, such as a proteinous factor or a nucleic acid that encodes the same (including forms incorporated in a vector), or a low molecular compound, as long as it is a substance (substances) capable of inducing a cell having pluripotency and self-replication competence from a somatic cell such as fibroblast. When the nuclear reprogramming factor is a proteinous factor or a nucleic acid that encodes the same, preferable nuclear reprogramming factors are exemplified by the following combinations (hereinafter, only the names for proteinous factors are shown).

(1) Oct3/4, Klf4, Sox2, c-Myc (wherein Sox2 is replaceable with Sox1, Sox3, Sox15, Sox17 or Sox18. Klf4 is replaceable with Klf1, Klf2 or Klf5. Furthermore, c-Myc is replaceable with T58A (active form mutant), N-Myc or L-Myc.)
(2) Oct3/4, Klf4, Sox2
(3) Oct3/4, Klf4, c-Myc
(4) Oct3/4, Sox2, Nanog, Lin28
(5) Oct3/4, Klf4, c-Myc, Sox2, Nanog, Lin28
(6) Oct3/4, Klf4, Sox2, bFGF
(7) Oct3/4, Klf4, Sox2, SCF
(8) Oct3/4, Klf4, c-Myc, Sox2, bFGF
(9) Oct3/4, Klf4, c-Myc, Sox2, SCF Among these combinations, when use of the obtained iPS cell for therapeutic application is considered, a combination of the three factors of Oct3/4, Sox2 and Klf4 is preferable. On the other hand, when use of the iPS cell for therapeutic application is not considered (e.g., used as an investigational tool for drug discovery screening and others), four factors consisting of Oct3/4, Klf4, Sox2 and c-Myc, or 5 factors by adding Lin28 or Nanog thereto are preferable.

iPS cell is preferably used for autologous transplantation.

A pluripotent stem cell obtained by modifying genes in a chromosome by a known genetic engineering method can also be used in the present invention. The pluripotent stem cell may be a cell wherein a labeling gene (e.g., fluorescent protein such as GFP etc.) has been knocked in a gene encoding a differentiation marker in an in-frame manner by a known method, which cell can be identified to have reached the corresponding differentiation stage by using the expression of the labeling gene as an index.

As the pluripotent stem cell, warm-blooded animal pluripotent stem cells, preferably mammalian pluripotent stem cells, can be used. Mammals include, for example, laboratory animals, including rodents such as mice, rats, hamsters and guinea pigs, and rabbits; domestic animals such as pigs, cattle, goat, horses, and sheep; companion animals such as dogs and cats; primates such as humans, monkeys, orangutans, and chimpanzees. Pluripotent stem cell is preferably pluripotent stem cell of rodents (mouse, rat etc.) or primates (human etc.) and most preferably human pluripotent stem cell.

Pluripotent stem cells can be cultured for maintenance by a method known per se. For example, from the aspects of clinical application, pluripotent stem cells are preferably maintained by serum-free culturing using serum alternatives such as Knockout™ Serum Replacement (KSR), or feeder-free cell culturing.

The pluripotent stem cells to be used in the present invention are preferably isolated. Being "isolated" means that an operation to remove factors other than the target cell or component has been performed, and the cell or component is no longer in a natural state. The purity of the "isolated human pluripotent stem cells" (percentage of the number of human pluripotent stem cells to the total cell number) is generally not less than 70%, preferably not less than 80%, more preferably not less than 90%, further preferably not less than 99%, most preferably 100%.

(2) Formation of Pluripotent Stem Cell Aggregate

A pluripotent stem cell aggregate can be obtained by culturing dispersed pluripotent stem cells under conditions that are non-adhesive to the culture vessel (i.e., culturing in suspension), and assembling plural pluripotent stem cells to allow for aggregate formation.

A culture vessel used for the aggregate formation is not particularly limited, and examples thereof include flasks, tissue culture flasks, dishes, Petri dishes, tissue culture dishes, multi-dishes, microplates, micro-well plates, micropores, multi-well plates (384 well, 192 well, 96 well, 48 well, 24 well etc.), chamber slides, schale, tubes, trays, culture bags, and roller bottles. To enable culturing under non-adhesive conditions, the culture vessel is preferably non-cell-adherent. Useful non-cell-adherent culture vessels include culture vessels whose surfaces have been artificially treated to be cell non-adherent, and culture vessels whose surfaces have not undergone an artificial treatment for improving the cell adhesiveness (e.g., coating treatment with an extracellular matrix and others).

The shape of the bottom of the multiwell plate, micropore, chamber slide, tube and others is preferably U-bottom or V-bottom, most preferably V-bottom, to facilitate precipitation of the dispersed pluripotent stem cells on one spot. The V-bottom container refers to a container having a bottom surface with an inclined plane, where the inclined plane forms a uniform inclining angle (e.g., 30-60° from the water flat plane) over the whole bottom surface.

The medium to be used for aggregate formation can be prepared using a medium used for culturing mammalian cells as a basal medium. The basal medium is not particularly limited as long as it can be used for culturing mammalian cells and may be BME medium, BGJb medium, CMRL 1066 medium, Glasgow MEM medium, Improved MEM Zinc Option medium, IMDM medium, Medium 199 medium, Eagle MEM medium, αMEM medium, DMEM medium, ham medium, Ham's F-12 medium, RPMI 1640 medium, Fischer's medium, Neurobasal medium, a mixed medium thereof and others. In one embodiment, a mixed medium of IMDM medium and Ham's F-12 medium is used. The mixing ratio is, for example, IMDM:Ham's F-12=0.8-1.2:1.2-0.8, in a volume ratio.

The medium to be used for culturing may be a serum-containing medium or a serum-free medium. The serum-free medium means a medium free of an unadjusted or unpurified serum. A medium contaminated with purified components derived from blood and components derived from animal tissue (e.g., growth factor) corresponds to a serum-free medium. To avoid contamination with chemically-undefined components, a serum-free medium is preferably used in the present invention.

The medium used for aggregate formation may contain a serum alternative. The serum alternative can, for example, be one comprising as appropriate an albumin, transferrin, fatty acids, collagen precursor, trace elements, 2-mercaptoethanol or 3'-thiolglycerol, or their equivalents and others. Such a serum alternative can be prepared by, for example, a method described in WO98/30679. To facilitate easier implementation of the method of the present invention, commercially available serum alternatives can be utilized. Examples of such commercially available serum alternatives include Knockout Serum Replacement (KSR, produced by Life Technologies), and Chemically-defined Lipid Concentrated (produced by Life Technologies).

A medium to be used for aggregate formation can contain other additive as long as induction of differentiation of pluripotent stem cells into cerebellum or a progenitor tissue thereof is not adversely influenced. Examples of the additive include, but are not limited to, insulin, iron source (e.g., transferrin etc.), mineral (e.g., sodium selenate etc.), saccharides (e.g., glucose etc.), lipid (e.g., cholesterol etc.), organic acid (e.g., pyruvic acid, lactic acid etc.), serum protein (e.g., albumin etc.), amino acid (e.g., L-glutamine etc.), reducing agent (e.g., 2-mercaptoethanol, monothioglycerol etc.), vitamins (e.g., ascorbic acid, d-biotin etc.), antibiotic (e.g., streptomycin, penicillin, gentamicin etc.), buffering agent (e.g., HEPES etc.) and others.

A medium to be used for aggregate formation may be preferably a medium used in the below-mentioned step (I).

For formation of a pluripotent stem cell aggregate, pluripotent stem cells are collected from passage culture and dispersed to a single cell state or near single cell state. Pluripotent stem cells are dispersed with an appropriate cell dissociation solution. Examples of the cell dissociation solution include EDTA; protease such as trypsin, collagenase IV, and metalloproteinase, and others, which are used alone or in an appropriate combination. Of these, one showing low cell toxicity is preferable, and examples of such cell dissociation solution include commercially available products such as DISPASE (EIDIA), TryPLE (Life Technologies), and Accutase (MILLIPORE). The dispersed pluripotent stem cells are suspended in the above-mentioned medium.

To suppress cell death of pluripotent stem cells (particularly, human pluripotent stem cells) induced by dispersion, it is preferable to add an inhibitor of Rho-associated coiled-coil kinase (ROCK) from the start of cultivation (JP-A-2008-99662). While the period of addition of the ROCK inhibitor is not particularly limited as long as the cell death of the pluripotent stem cell can be suppressed, for example, it is added within a period of 15 days from the start of the cultivation. Examples of the ROCK inhibitor include Y-27632 ((+)-(R)-trans-4-(1-aminoethyl)-N-(4-pyridyl)cyclohexanecarboxamide dihydrochloride) and others. The concentration of the ROCK inhibitor used for suspension culturing is a concentration capable of suppressing cell death of pluripotent stem cells induced by dispersion. For example, for Y-27632, this concentration is normally about 0.1 to 200 μM, preferably about 2 to 50 μM. The concentration of the ROCK inhibitor may be changed in the addition period thereof and, for example, the concentration may be reduced to half in the latter half period.

To suppress cell death of pluripotent stem cells (particularly, human pluripotent stem cells) induced by dispersion, a ROCK inhibitor may be added to the aforementioned cell dissociation solution and pluripotent stem cells may be dispersed in the presence of the ROCK inhibitor.

A suspension of the dispersed pluripotent stem cells is seeded in the above-mentioned culture vessel and the dispersed pluripotent stem cells are cultured under conditions that are non-adhesive to the cell culture vessel, whereby the plural pluripotent stem cells are assembled to form an aggregate. In this case, dispersed pluripotent stem cells may be seeded in a comparatively large culture vessel such as a 10-cm dish to simultaneously form plural pluripotent stem cell aggregates in one culture compartment. However, the size of aggregates, and the number of pluripotent stem cells contained in the aggregate may vary widely, and such variation may cause difference in the levels of differentiation of pluripotent stem cells into cerebellum or a progenitor tissue thereof between aggregates, which in turn may lower the efficiency of differentiation induction. Therefore, it is preferable to rapidly coagulate the dispersed pluripotent stem cells to form one aggregate in one culture compartment. Examples of the method for rapidly ss coagulating the dispersed pluripotent stem cells include the following methods:

(1) A method including enclosing dispersed pluripotent stem cells in a culture compartment having a comparatively small volume (e.g., not more than 1 ml, not more than 500 μl, not more than 200 μl, not more than 100 μl) to form one aggregate in the compartment. Preferably, the culture compartment is stood still after enclosing the dispersed pluripotent stem cells. Examples of the culture compartment include, but are not limited to, a well in a multi-well plate (384-well, 192-well, 96-well, 48-well, 24-well etc.), micropore, chamber slide and others; tube; and a droplet of a medium in hanging drop method. The dispersed pluripotent stem cells enclosed in the compartment are precipitated on one spot due to the gravity, or the cells adhere to each other to form one aggregate in one culture compartment. The shape of the bottom of the multiwall plate, micropore, chamber slide, tube and others is preferably U-bottom or V-bottom, most preferably V-bottom, to facilitate precipitation of the dispersed pluripotent stem cells on one spot.

(2) A method including placing dispersed pluripotent stem cells in a centrifugation tube, centrifuging same to allow for precipitation of pluripotent stem cells on one spot, thereby forming one aggregate in the tube.

The number of pluripotent stem cells to be seeded in one culture compartment is not particularly limited as long as one aggregate is formed per one culture compartment, and differentiation of pluripotent stem cells into cerebellum or a progenitor tissue thereof can be induced in the aggregate by the method of the present invention. Generally, about $1 \times 10^3$-about $5 \times 10^4$, preferably about $1 \times 10^3$-about $2 \times 10^4$, more preferably about $2 \times 10^3$-about $1.2 \times 10^4$, further preferably about $5 \times 10^3$-about $7 \times 10^3$ (e.g., 6000) of pluripotent stem cells are seeded in one culture compartment. Then, by rapidly coagulating the pluripotent stem cells, one cell aggregate generally composed of about $1 \times 10^3$-about $5 \times 10^4$, preferably about $1 \times 10^3$-about $2 \times 10^4$, more preferably about $2 \times 10^3$-about $1.2 \times 10^4$, further preferably about $5 \times 10^3$-about $7 \times 10^3$ (e.g., 6000) pluripotent stem cells is formed per one culture compartment.

The time up to aggregate formation can be determined as appropriate as long as one aggregate is formed per one compartment, and differentiation of pluripotent stem cells into cerebellum or a progenitor tissue thereof can be induced in the aggregate by the method of the present invention. By shortening the time, efficient induction of differentiation into the object cerebellum or a progenitor tissue thereof is expected, and therefore, said time is preferably shorter. Preferably, pluripotent stem cell aggregate is formed within 24 hr, more preferably within 12 hr, further preferably within 6 hr, most preferably in 2-3 hr. The time up to the aggregate formation can be adjusted as appropriate by choosing a tool for cell aggregation, centrifugal conditions and others by those skilled in the art.

Other culturing conditions such as culturing temperature and $CO_2$ concentration at the time of aggregate formation can be set as appropriate. The culturing temperature is not particularly limited, and is, for example, about 30 to 40° C., preferably about 37° C. The $CO_2$ concentration is, for example, about 1 to 10%, preferably about 5%.

Furthermore, multiple culture compartments under the same culturing conditions are prepared and one pluripotent stem cell aggregate is formed in each culture compartment, whereby a qualitatively uniform population of pluripotent stem cell aggregates can be obtained. Whether pluripotent stem cell aggregates are qualitatively uniform can be evaluated on the basis of the size of the aggregate mass and the number of cells therein, macroscopic morphology, microscopic morphology and homogeneity thereof as analyzed by histological staining, the expression of differentiation and un-differentiation markers and homogeneity thereof, the regulation of the expression of differentiation markers and synchronicity thereof, reproducibility of differentiation efficiency among aggregates, and others. In one embodiment, a population of the pluripotent stem cell aggregates to be used in the method of the present invention contains a uniform number of pluripotent stem cells in the aggregates. A population of pluripotent stem cell aggregates being "uniform" in a particular parameter means that not less than 90% of the total aggregates in a population thereof falls within the range of mean of the parameter in the aggregate population ±10%, preferably ±5%.

(3) Induction of Cerebellar Progenitor Tissue

The present invention provides a method for producing a human cell aggregate comprising a cerebellar progenitor tissue, comprising subjecting an aggregate of pluripotent stem cells to suspension culturing in a serum-free medium containing insulin, and treating, in the suspension culturing, the aggregate of human pluripotent stem cells or a human cell aggregate derived therefrom with a ROCK inhibitor, a TGFβ signal inhibitor, and a first fibroblast growth factor.

Examples of the cerebellar progenitor tissue include, but are not limited to, a midbrain-hindbrain boundary neural progenitor tissue; a cerebellar plate tissue; a partial tissue thereof (e.g., ventricular zone, rhombic lip) and others. The midbrain-hindbrain boundary is an organizer that controls the development of the midbrain and the anterior hindbrain during the process of embryogenesis. The midbrain-hindbrain boundary can be identified by the expression of the midbrain-hindbrain boundary marker. As the midbrain-hindbrain boundary marker, En2 (midbrain marker), Gbx2 (rostral hindbrain marker) and others can be mentioned. The midbrain-hindbrain boundary comprises at least one selected from the group consisting of an En2 positive neural progenitor and a Gbx2 positive neural progenitor, preferably both cells. The neural progenitor can be identified as an N-cadherin positive cell. In one embodiment, the midbrain-hindbrain boundary is an En2 positive and/or Gbx2 positive neural progenitor tissue. The definition of the cerebellar plate tissue is mentioned below.

In the present invention, the tissue refers to a structure of a cell population having a structure in which plural kinds of cells having different forms and properties are sterically arranged in a certain pattern.

The production method of the present invention specifically comprises subjecting an aggregate of pluripotent stem cells to suspension culturing in a serum-free medium containing insulin, and treating, in the suspension culturing, the aggregate of human pluripotent stem cells or a human cell aggregate derived therefrom with a ROCK inhibitor, a TGFβ signal inhibitor, and a first fibroblast growth factor, to obtain a cell aggregate containing a midbrain-hindbrain boundary neural progenitor tissue (step (I)). When further progress of cerebellar differentiation is desired, the cell aggregate containing the midbrain-hindbrain boundary neural progenitor tissue obtained in step (I) is further subjected to suspension culturing in a serum-free medium to induce formation of a neuroepithelial structure by neural progenitors in the neural progenitor tissue, whereby the human cell aggregate containing the cerebellar plate tissue is obtained (step (II)). In step (I), differentiation of pluripotent stem cells into a midbrain-hindbrain boundary neural progenitor tissue is induced, and in step (II), further differentiation of a midbrain-hindbrain boundary neural progenitor tissue into a cerebellar plate tissue is induced.

Since self-organization of the cerebellar progenitor tissue is induced in a cell aggregate in the method of the present invention, the differentiation stage of cerebellar progenitor tissue contained in the cell aggregate proceeds with the progress of time. Therefore, the culturing period and culturing conditions are preferably adjusted as appropriate according to the differentiation stage of the intended cerebellar progenitor tissue.

(3.1) Step (I)

In step (I), an aggregate of pluripotent stem cells is subjected to suspension culturing in a serum-free medium containing insulin, and the aggregate of the pluripotent stem cells or a human cell aggregate derived therefrom is treated with a ROCK inhibitor, a TGFβ signal inhibitor, and a first fibroblast growth factor in the suspension culturing.

The "suspension culturing" of the pluripotent stem cell aggregate refers to culturing an aggregate of pluripotent stem cells in a medium under conditions that are non-adhesive to the culture vessel.

The medium used for the suspension culturing contains insulin. The concentration of insulin in the medium can be appropriately determined within a range in which differentiation of pluripotent stem cells into midbrain-hindbrain boundary neural progenitor tissue can be induced in the cell aggregate. The concentration thereof is generally not less than 0.1 μg/ml, preferably not less than 1 μg/ml. While the upper limit is not particularly set as long as there is no adverse effect on the differentiation into the midbrain-hindbrain boundary neural progenitor tissue, it is generally not more than 100 μg/ml, preferably not more than 20 μg/ml from the aspect of culturing cost. In one embodiment, the concentration of insulin in the medium is generally 0.1-100 μg/ml, preferably 1-20 μg/ml (e.g., 7 μg/ml). Since insulin particularly contributes to the promotion of proliferation of pluripotent stem cells or cells derived therefrom, it is contained in the medium at a concentration capable of achieving this effect.

The medium to be used for suspension culturing can be prepared using a medium used for culturing mammalian cells as a basal medium. The basal medium is not particularly limited as long as it can be used for culturing mammalian cells and may be BME medium, BGJb medium, CMRL 1066 medium, Glasgow MEM medium, Improved MEM Zinc Option medium, IMDM medium, Medium 199 medium, Eagle MEM medium, αMEM medium, DMEM medium, ham medium, Ham's F-12 medium, RPMI 1640 medium, Fischer's medium, Neurobasal medium, a mixed medium thereof and others. In one embodiment, a mixed medium of IMDM medium and Ham's F-12 medium is used. The mixing ratio is, for example, IMDM:Ham's F-12=0.8-1.2:1.2-0.8, in a volume ratio.

To avoid contamination with chemically-undefined components, a serum-free medium is preferably used for culturing in suspension.

The medium used for suspension culturing of a cell aggregate may contain a serum alternative. The serum alternative can, for example, be one comprising as appropriate an albumin, transferrin, fatty acids, trace elements, 2-mercaptoethanol or 3'-thiolglycerol, or their equivalents and others. Such a serum alternative can be prepared by, for example, a method described in WO98/30679. To facilitate easier implementation of the method of the present invention, commercially available serum alternatives can be utilized. Examples of such commercially available serum alternatives include Chemically-defined Lipid Concentrated (produced by Life Technologies). A serum alternative containing chemically-defined components is preferable. In addition, a serum alternative that does not contain a component isolated from an animal different from the animal species of the cell to be cultured (xenogeneic animal-derived component) (e.g., component isolated from a non-human animal when human cell is cultured) is preferable. Since a chemically-undefined serum alternative and a serum alternative containing xenogeneic animal-derived component (e.g., KSR (Knockout serum replacement)) may inhibit induction of differentiation of pluripotent stem cells into a midbrain-hindbrain boundary neural progenitor tissue, use thereof is not preferable.

The medium used for the suspension culturing of cell aggregate can contain other additive as long as induction of differentiation of pluripotent stem cells into midbrain-hindbrain boundary neural progenitor tissue is not adversely influenced. Examples of the additive include, but are not limited to, iron source (e.g., transferrin etc.), mineral (e.g., sodium selenate etc.), saccharides (e.g., glucose etc.), lipid (e.g., cholesterol etc.), organic acid (e.g., pyruvic acid, lactic acid etc.), serum protein (e.g., albumin etc.), amino acid (e.g., L-glutamine etc.), reducing agent (e.g., 2-mercaptoethanol, monothioglycerol etc.), vitamins (e.g., ascorbic acid, d-biotin etc.), antibiotic (e.g., streptomycin, penicillin, gentamicin etc.), buffering agent (e.g., HEPES etc.) and others.

In one embodiment, to avoid an adverse influence on the induction of differentiation into midbrain-hindbrain boundary neural progenitor tissue, the medium used for the suspension culturing of cell aggregates is desirably free of a growth factor other than those particularly described in the present specification to be contained in a medium. The "growth factor" here encompasses a pattern formation factor such as Fgf; BMP; Wnt, Nodal, Notch, and Shh; Lipid-rich albumin; extracellular matrix. Examples of the medium free of a growth factor include gfCDM disclosed in Wataya et al, Proc Natl Acad Sci USA, 105(33): 11796-11801, 2008.

To avoid contamination with a chemically-undefined component, a medium used for the suspension culturing is preferably a medium whose components are chemically-defined.

Preferably, a medium used for the suspension culturing does not contain a xenogeneic animal-derived component.

Other culturing conditions for suspension culturing of the cell aggregates, such as culturing temperature, $CO_2$ concentration and $O_2$ concentration, can be set as appropriate. The culturing temperature is, for example, about 30 to 40° C., preferably about 37° C. The $CO_2$ concentration is, for example, about 1 to 10%, preferably about 5%. The $O_2$ concentration is, for example, about 20%.

In the suspension culturing of step (I), the suspension culturing of the cell aggregate may be performed in the presence or absence of feeder cells as long as induction of differentiation of pluripotent stem cells into cerebellar progenitor tissue is possible by the method of the present invention. To avoid contamination with undefined factors, the suspension culturing of cell aggregate is preferably performed in the absence of feeder cells.

As a vessel that can be used for suspension culturing of a cell aggregate, those recited as vessels that can be used for forming the aggregate of pluripotent stem cells in (2) above can be mentioned. To stably position the cell aggregate in one place and avoid collapse of the aggregate, form of the bottom of the container is preferably U-bottom or V-bottom, most preferably V-bottom.

In a preferable embodiment, a qualitatively uniform population of pluripotent stem cell aggregates is cultured in suspension in a serum-free medium containing insulin. Using a qualitatively uniform population of pluripotent stem cell aggregates, difference in levels of differentiation into midbrain-hindbrain boundary neural progenitor tissue between aggregates can be suppressed to the minimum, and the efficiency of the intended differentiation induction can be improved. Suspension culturing of a qualitatively uniform population of pluripotent stem cell aggregates encompasses the following embodiments.

(1) Multiple culture compartments are prepared, and a qualitatively uniform population of pluripotent stem cell aggregates is seeded such that one pluripotent stem cell aggregate is contained in one culture compartment (e.g., one pluripotent stem cell aggregate is placed in each well of 96 well plate). In each culture compartment, one pluripotent stem cell aggregate is cultured in suspension in a medium containing insulin.

(2) A qualitatively uniform population of pluripotent stem cell aggregates is seeded such that plural pluripotent stem cell aggregates are contained in one culture compartment (e.g., plural pluripotent stem cell aggregates are placed in a 10 cm dish). In the culture compartment, plural pluripotent stem cell aggregates are cultured in suspension in a medium containing insulin.

Any of the embodiments (1) and (2) may be employed for the method of the present invention and the embodiment may be changed during culturing (from embodiment (1) to embodiment (2), or from embodiment (2) to embodiment (1)). In one embodiment, the embodiment (1) is employed in step (I) and the embodiment of is employed in step (II).

In step (I), an aggregate of pluripotent stem cells or a human cell aggregate derived therefrom is treated with a ROCK inhibitor, a TGFβ signal inhibitor, and a first fibroblast growth factor in the above-mentioned suspension culturing. The treatment of the cell aggregate with these factors can be achieved by adding a ROCK inhibitor, a TGFβ signal inhibitor, and a first fibroblast growth factor to the suspension culturing, and bringing the pluripotent stem cell aggregate or a cell aggregate derived therefrom into contact with the ROCK inhibitor, the TGFβ signal inhibitor, and the first fibroblast growth factor in the medium.

The Rho-associated coiled-coil kinase (ROCK) inhibitor has an effect of suppressing cell death of the pluripotent stem cell (particularly, human pluripotent stem cell) induced by dispersion, and supporting the growth. As a ROCK inhibitor, several compounds are known (e.g., Ishizaki et al., Mol. Pharmacol. 57, 976-983 (2000) and Narumiya et al., Methods Enzymol. 325, 273-284 (2000)). Specifically, as a ROCK inhibitor, Y-27632 ((+)-(R)-trans-4-(1-aminoethyl)-N-(4-pyridyl)cyclohexanecarboxamide) (preferably, dihydrochloride); Fasudil (5-(1-Homopiperazinyl)sulfonylisoquinoline) (preferably, hydrochloride); H-1152((S)-(+)-2-Methyl-1-[(4-methyl-5-isoquinolinyl) sulfonyl]-hexahydro-1H-1,4-diazepine) (preferably, dihydrochloride) and others can be mentioned. The ROCK inhibitor is preferably Y-27632.

The timing and duration of the treatment of the cell aggregate with a ROCK inhibitor are not particularly limited as long as the cell death of the pluripotent stem cells, which is induced by dispersion, can be suppressed and differentiation of pluripotent stem cells into midbrain-hindbrain boundary neural progenitor tissue is possible. To effectively suppress cell death of the pluripotent stem cells, which is induced by dispersion, a ROCK inhibitor is added to the medium preferably within 2 hr from the start of the suspension culturing, more preferably within 0.5 hr from the start of the suspension culturing, further preferably from the start of the suspension culturing, of the pluripotent stem cell aggregate, to treat the cell aggregate with the ROCK inhibitor. The treatment period with the ROCK inhibitor is generally not less than 12 hr, preferably not less than 2, 4, or 7 days. The upper limit of the treatment period with the ROCK inhibitor is not particularly set as long as differentiation of pluripotent stem cells into midbrain-hindbrain boundary neural progenitor tissue is possible. To avoid an unpredictable adverse influence on the differentiation, it is generally within 21 days, preferably within 14 days. After lapse of the treatment period with the ROCK inhibitor, the ROCK inhibitor is removed from the medium. The concentration of the ROCK inhibitor in the medium during the treatment with the ROCK inhibitor is a concentration capable of suppressing cell death of pluripotent stem cells, which is induced by dispersion. For example, for Y-27632, this concentration is generally about 0.1 to 200 μM, preferably about 2 to 50 μM. The concentration of the ROCK inhibitor may be varied in the period of treatment. For example, the concentration can be reduced to half in the latter half period.

A TGFβ signal inhibitor has an effect of suppressing differentiation of pluripotent stem cells into mesoderm, and promoting differentiation into neuroectoderm. The TGFβ signal inhibitor is not particularly limited as long as it is capable of suppressing the signal transduction mediated by TGFβ. Examples of the TGFβ signal inhibitor include, but are not limited to, SB431542 (4-(5-benzol[1,3]dioxol-5-yl-4-pyridin-2-yl-1H-imidazol-2-yl)-benzamide), LY-364947, SB-505, A-83-01 and others. Particularly, SB431542 is preferable.

The timing and duration of the treatment of the cell aggregate with a TGFβ signal inhibitor are not particularly limited as long as differentiation of pluripotent stem cells into mesoderm can be suppressed, and differentiation into neuroectoderm can be promoted. To effectively suppress mesoderm differentiation and effectively promote differentiation into neuroectoderm, a TGFβ signal inhibitor is added to the medium preferably within 2 hr from the start of the suspension culturing, more preferably within 0.5 hr from the start of the suspension culturing, further preferably from the start of the suspension culturing, of an aggregate of pluripotent stem cells, to treat the cell aggregate with the TGFβ signal inhibitor. The treatment period with the TGFβ signal inhibitor is generally not less than 2 days, preferably not less than 7 days. The upper limit of the treatment period with the TGFβ signal inhibitor is not particularly set as long as differentiation of pluripotent stem cells into midbrain-hindbrain boundary neural progenitor tissue is possible. To avoid an unpredictable adverse influence on the differentiation, it is generally within 21 days, preferably within 14 days. After lapse of the treatment period with the TGFβ signal inhibitor, the TGFβ signal inhibitor is removed from the medium. The concentration of TGFβ signal inhibitor in the medium during the treatment with the TGFβ signal inhibitor is a concentration capable of suppressing differentiation of pluripotent stem cells into mesoderm and capable of promoting differentiation into neuroectoderm. For example, for SB431542, this concentration is generally about 0.1 to 200 µM, preferably about 2 to 50 µM, more preferably about 10-30 µM. The concentration of the TGFβ signal inhibitor may be varied in the period of treatment. For example, the concentration can be reduced to half in the latter half period.

The first fibroblast growth factor is an FGF having an effect of promoting differentiation of pluripotent stem cells into midbrain-hindbrain boundary and suppressing differentiation into forebrain. The fibroblast growth factor is not particularly limited as long as it promotes differentiation into midbrain-hindbrain boundary. As the fibroblast growth factor (FGF), FGF1-FGF23 have been identified in human and mouse. Since human FGF19 is an ortholog of mouse FGF15, the FGF family of human and mouse is constituted of 22 members. In the present specification, the name of FGF follows the nomenclature of human FGF. The first fibroblast growth factor is preferably FGF2 or FGF8, more preferably FGF2. FGF2 is a known cytokine also called basic fibroblast growth factor (bFGF), and its amino acid sequence is also known. FGF2 to be used in the present invention is generally mammalian FGF2. Examples of the mammal include those mentioned above. Since FGF2 has cross-reactivity among many mammalian species, FGF2 of any mammal may also be used as long as the object of the present invention can be achieved. Preferably, FGF2 of a mammal of the same species as the cell to be cultured is used. For example, FGF2 of rodents (mouse, rat etc.) or primates (human etc.) is used. Here, mouse FGF2 means that FGF2 has the amino acid sequence of FGF2 naturally expressed in the body of mouse. In the present specification, similar interpretation is also applied to other proteins and others. Examples of the representative amino acid sequence of mouse FGF2 include NCBI accession No. NP_032032.1 (updated Feb. 18, 2014), an amino acid sequence obtained by removing the N-terminus signal sequence (1-9) from said amino acid sequence (mature mouse FGF2 amino acid sequence) and others. Examples of the representative amino acid sequence of human FGF2 include NCBI accession No. NP_001997.5 (updated Feb. 18, 2014) and others.

The timing and duration of the treatment of the cell aggregate with the first fibroblast growth factor are not particularly limited as long as differentiation of pluripotent stem cells into midbrain-hindbrain boundary region can be promoted. When the start of the suspension culturing of the pluripotent stem cell aggregate is taken as day 0 (d0), the first fibroblast growth factor is added to the medium preferably at any time point in d2-d4, more preferably d2, to start the treatment of the cell aggregate with the first fibroblast growth factor. The treatment period with the first fibroblast growth factor is generally not less than 2 days, preferably not less than 5 days. The upper limit of the treatment period with the first fibroblast growth factor is not particularly set as long as differentiation of pluripotent stem cells into midbrain-hindbrain boundary neural progenitor tissue is possible. To avoid an unpredictable adverse influence on the differentiation, it is generally within 19 days, preferably within 12 days. After lapse of the treatment period with the first fibroblast growth factor, the first fibroblast growth factor is removed from the medium. The concentration of the first fibroblast growth factor in the medium during the treatment with the first fibroblast growth factor is a concentration capable of promoting differentiation of pluripotent stem cells into midbrain-hindbrain boundary. While the first fibroblast growth factor is also used for maintenance culturing of pluripotent stem cells, the concentration for promoting differentiation into midbrain-hindbrain boundary is generally higher than that for maintenance culturing. When FGF2 is used as the first fibroblast growth factor, the concentration thereof in the medium is preferably not less than 20 ng/ml, more preferably not less than 40 ng/ml, further preferably not less than 50 ng/ml. While the upper limit of the FGF2 concentration is not particularly set as long as no adverse effect on the differentiation into midbrain-hindbrain boundary is found, it is preferably not more than 1000 ng/ml, more preferably not more than 300 ng/ml, further preferably not more than 100 ng/ml, from the aspects of culturing costs. In one embodiment, the concentration of FGF2 in the medium is preferably 20-1000 ng/ml, preferably 40-300 ng/ml, further preferably 50-100 ng/ml. The concentration of the first fibroblast growth factor may be varied in the period of treatment. For example, the concentration can be reduced to half in the latter half period.

In a preferable embodiment, the cell aggregate is not stimulated with the first fibroblast growth factor from the start of the suspension culturing up to the start of the treatment with the first fibroblast growth factor. That is, the medium for the suspension culturing is preferably substantially free of the first fibroblast growth factor from the start of the suspension culturing up to the start of the treatment with the first fibroblast growth factor. Being "substantially free of the first fibroblast growth factor" means that the concentration of the first fibroblast growth factor in the medium is lower than the concentration for promoting differentiation into midbrain-hindbrain boundary. In one embodiment, the concentration of the first fibroblast growth factor in the medium during the period of from the start of the suspension culturing to the start of the treatment with the first fibroblast growth factor is generally less than 1 ng/ml, preferably less than 0.1 ng/ml, more preferably less than 0.01 ng/ml.

In one embodiment, step (I) comprises further treating the aggregate of human pluripotent stem cells or a human cell aggregate derived therefrom with a second fibroblast growth factor in the suspension culturing.

The second fibroblast growth factor is an FGF having an effect to confer polarity along the dorsal-ventral axis of neural tube upon the neuroepithelial structure formed in step (II), which is conducted using the cell aggregate obtained step (I). As the fibroblast growth factor (FGF), FGF1-FGF23 have been identified in human and mouse. The second fibroblast growth factor is preferably FGF19, FGF17 or FGF8, more preferably FGF19. FGF19 is a known cytokine, and its amino acid sequence is also known. FGF19 to be used in the present invention is generally mammalian FGF19. Examples of the mammal include those mentioned above. FGF19 of any mammal may also be used as long as the object of the present invention can be achieved. Preferably, FGF19 of a mammal of the same species as the cell to be cultured is used. For example, FGF19 of rodents (mouse, rat etc.) or primates (human etc.) is used. Examples of the representative amino acid sequence of human FGF19 include NCBI accession No. NP_0015108.1 (updated Apr. 27, 2014), an amino acid sequence obtained by removing the N-terminus signal sequence (1-22) from said amino acid sequence (mature human FGF19) and others.

The timing and duration of the treatment of the cell aggregate with the second fibroblast growth factor are not particularly limited as long as polarity along the dorsal-ventral axis of neural tube is conferred upon the neuroepithelial structure. When the start of the suspension culturing of the pluripotent stem cell aggregate is taken as day 0 (d0), the second fibroblast growth factor is added to the medium preferably at any time point in d10-d14, more preferably d14, to start the treatment of the cell aggregate with the second fibroblast growth factor. The treatment period with the second fibroblast growth factor is generally not less than 2 days, preferably not less than 4 days. The upper limit of the treatment period with the second fibroblast growth factor is not particularly limited as long as polarity along the dorsal-ventral axis of neural tube is conferred upon the neuroepithelial structure. To suppress possibility of differentiating into a moiety other than the midbrain-hindbrain boundary, it is generally within 14 days, preferably within 11 days, more preferably within 7 days. After the treatment period with the second fibroblast growth factor, the second fibroblast growth factor is removed from the medium. The concentration of the second fibroblast growth factor in the medium in the second fibroblast growth factor treatment period is a concentration that confers polarity along the dorsal-ventral axis of neural tube upon the neuroepithelial structure. When FGF19 is used as the second fibroblast growth factor, the concentration thereof in the medium is preferably not less than 30 ng/ml, more preferably not less than 40 ng/ml, further preferably not less than 50 ng/ml. While the upper limit of FGF19 concentration is not particularly set as long as no adverse effect on the differentiation into midbrain-hindbrain boundary is found, it is preferably not more than 1000 ng/ml, more preferably not more than 500 ng/ml, more preferably not more than 300 ng/ml. In one embodiment, the concentration of FGF2 in the medium is preferably 30-1000 ng/ml, preferably 40-500 ng/ml, more preferably 50-300 ng/ml. The concentration of the second fibroblast growth factor may be varied in the period of treatment. For example, the concentration can be reduced to half in the latter half period.

In a preferable embodiment, the cell aggregate is not stimulated with the second fibroblast growth factor from the start of the suspension culturing up to the start of the treatment with the second fibroblast growth factor. That is, the medium for the suspension culturing is preferably substantially free of the second fibroblast growth factor from the start of the suspension culturing up to the start of the treatment with the second fibroblast growth factor. Being "substantially free of the second fibroblast growth factor" means that the concentration of the second fibroblast growth factor in the medium is lower than the concentration for conferring polarity along the dorsal-ventral axis of neural tube upon the neuroepithelial structure. In one embodiment, the concentration of the second fibroblast growth factor in the medium during the period from the start of the suspension culturing to the start of the treatment with the second fibroblast growth factor is generally less than 1 ng/ml, preferably less than 0.1 ng/ml, more preferably less than 0.01 ng/ml, most preferably 0 ng/ml.

Insulin, the first fibroblast growth factor and the second fibroblast growth factor to be used in the present invention are preferably isolated. Being "isolated" means that an operation to remove factors other than the intended component or cell has been performed, and the component or cell is no longer in a natural state. Therefore, "isolated protein X" does not include an endogenous protein X produced from the cell or tissue to be cultured. The purity of the "isolated protein X" (percentage of the weight of protein X to the total protein weight) is generally not less than 70%, preferably not less than 80%, more preferably not less than 90%, further preferably not less than 99%, most preferably 100%. The isolated insulin, the first fibroblast growth factor and the second fibroblast growth factor contained in a medium used for the suspension culturing was exogenously added to the medium. Therefore, in one embodiment, the present invention comprises a step of providing each of isolated insulin/isolated first fibroblast growth factor/isolated second fibroblast growth factor. In one embodiment, a step of exogenously adding each of isolated insulin/isolated first fibroblast growth factor/isolated second fibroblast growth factor to the medium used for suspension culturing in step (I) is comprised.

A preferable combination of a ROCK inhibitor, a TGFβ signal inhibitor and the first fibroblast growth factor is Y27632, SB431542 and FGF2.

A preferable combination of a ROCK inhibitor, a TGFβ signal inhibitor, the first fibroblast growth factor and the second fibroblast growth factor is Y27632, SB431542, FGF2 and FGF19.

In one embodiment, in the suspension culturing in step (I), the aggregate of pluripotent stem cells or a human cell aggregate derived therefrom is treated with a ROCK inhibitor from the start of the suspension culturing, treated with a TGFβ signal inhibitor from the start of the suspension culturing, and treated with the first fibroblast growth factor from day 2-4 after the start of the suspension culturing. The treatment period with the ROCK inhibitor is a period sufficient for suppressing cell death of pluripotent stem cells, which is induced by dispersion (e.g., for 12 hr (2 days, 4 days, or 7 days)-21 days (or 14 days)). The treatment period with the TGFβ signal inhibitor is a period sufficient for suppressing mesoderm differentiation and promoting differentiation into neuroectoderm (e.g., for 2 days (or 7 days)-21 days (or 14 days)). The treatment period with the first fibroblast growth factor treatment is a period sufficient for promoting differentiation of pluripotent stem cells into midbrain-hindbrain boundary neural progenitor tissue (e.g., for 2 days (or 5 days)-19 days (or 12 days)).

In one embodiment, in the suspension culturing in step (I), the aggregate of pluripotent stem cells or a human cell aggregate derived therefrom is treated with a ROCK inhibitor from the start of the suspension culturing, treated with a TGFβ signal inhibitor from the start of the suspension culturing, treated with the first fibroblast growth factor from day 2-4 after the start of the suspension culturing, and treated with the second fibroblast growth factor from day 10-14 after the start of the suspension culturing. The treatment period with the ROCK inhibitor is a period sufficient for suppressing cell death of pluripotent stem cells, which is induced by dispersion (e.g., for 12 hr (2 days, 4 days, or 7 days)-21 days (or 14 days)). The treatment period with the TGFβ signal inhibitor is a period sufficient for suppressing mesoderm differentiation and promoting differentiation into neuroectoderm (e.g., for 2 days (or 7 days)-21 days (or 14 days)). The treatment period with the first fibroblast growth factor is a period sufficient for promoting differentiation of pluripotent stem cells into midbrain-hindbrain boundary neural progenitor tissue (e.g., for 2 days (or 5 days)-19 days (or 12 days)). The treatment period with the second fibroblast growth factor treatment is a period sufficient for conferring polarity along dorsal-ventral axis of the neural tube upon the neuroepithelial structure (e.g., for 2 days (or 4 days)-14 days (or 11 days or 7 days)).

In a preferable embodiment, for formation of an aggregate of pluripotent stem cells in (2) above, the medium used in step (I) is used to form an aggregate of pluripotent stem cells, and the suspension culturing of the aggregate is continued to perform step (I). That is, the dispersed pluripotent stem cells are suspended in a medium (serum-free medium containing insulin) to be used in step (I), a suspension of the dispersed pluripotent stem cells is seeded in the above-mentioned culture vessel and the dispersed pluripotent stem cells are cultured under conditions that are non-adhesive to the cell culture vessel, whereby the plural pluripotent stem cells are assembled to form an aggregate, and the formed pluripotent stem cell aggregate is continuously cultured in suspension in the same medium. Since the dispersed pluripotent stem cells form aggregates in a short time when suspension culturing is started, in this embodiment, the start of the culturing of the dispersed pluripotent stem cells can be regarded as the start of the suspension culturing in step (I).

In one embodiment, pluripotent stem cells dispersed in a serum-free medium containing insulin, a ROCK inhibitor and a TGFβ signal inhibitor are subjected to suspension culturing in a culture vessel to form a pluripotent stem cell aggregate, and the obtained pluripotent stem cell aggregate is continuously cultured in suspension in the same serum-free medium. In the suspension culturing, the aggregate of pluripotent stem cells or a human cell aggregate derived therefrom is further treated with the first fibroblast growth factor (and optionally the second fibroblast growth factor).

In one embodiment, pluripotent stem cells dispersed in a serum-free medium containing insulin, a ROCK inhibitor and a TGFβ signal inhibitor are subjected to suspension culturing to form a pluripotent stem cell aggregate, and the obtained pluripotent stem cell aggregate is continuously cultured in suspension in the same serum-free medium. In this suspension culturing, the aggregate of pluripotent stem cells or a cell aggregate derived therefrom is further treated with the first fibroblast growth factor from day 2-4 after the start of the suspension culturing. The treatment period with the ROCK inhibitor is a period sufficient for suppressing cell death of pluripotent stem cells, which is induced by dispersion (e.g., for 12 hr (2 days, 4 days, or 7 days)-21 days (or 14 days)). The treatment period with the TGFβ signal inhibitor is a period sufficient for suppressing mesoderm differentiation and promoting differentiation into neuroectoderm (e.g., for 2 days (or 7 days)-21 days (or 14 days)). The treatment period with the first fibroblast growth factor treatment is a period sufficient for promoting differentiation of pluripotent stem cells into midbrain-hindbrain boundary neural progenitor tissue (e.g., for 2 days (or 5 days)-19 days (or 12 days)).

In one embodiment, pluripotent stem cells dispersed in a serum-free medium containing insulin, a ROCK inhibitor and a TGFβ signal inhibitor are subjected to suspension culturing to form a pluripotent stem cell aggregate, and the obtained pluripotent stem cell aggregate is continuously cultured in suspension in the same serum-free medium. In this suspension culturing, the aggregate of pluripotent stem cells or a cell aggregate derived therefrom is treated with the first fibroblast growth factor from day 2-4 after the start of the suspension culturing, and treated with the second fibroblast growth factor from day 10-14 after the start of the suspension culturing. The treatment period with the ROCK inhibitor is a period sufficient for suppressing cell death of pluripotent stem cells, which is induced by dispersion (e.g., for 12 hr (2 days, 4 days, or 7 days)-21 days (or 14 days)). The treatment period with the TGFβ signal inhibitor is a period sufficient for suppressing mesoderm differentiation and promoting differentiation into neuroectoderm (e.g., for 2 days (or 7 days)-21 days (or 14 days)). The treatment period with the first fibroblast growth factor is a period sufficient for promoting differentiation of pluripotent stem cells into midbrain-hindbrain boundary neural progenitor tissue (e.g., for 2 days (or 5 days)-19 days (or 12 days)). The treatment period with the second fibroblast growth factor is a period sufficient for conferring polarity along dorsal-ventral axis of the neural tube upon the neuroepithelial structure (e.g., for 2 days (or 4 days)-14 days (or 11 days or 7 days)).

The suspension culturing in step (I) is performed for a period sufficient for inducing differentiation of pluripotent stem cells into midbrain-hindbrain boundary neural progenitor tissue. As a result, the cell aggregate containing the midbrain-hindbrain boundary neural progenitor tissue is obtained. The differentiation into midbrain-hindbrain boundary neural progenitor tissue can be detected by, for example, RT-PCR using a midbrain-hindbrain boundary marker specific probe, and immunohistochemistry using a midbrain-hindbrain boundary marker specific antibody and neural progenitor tissue specific antibody. For example, the suspension culturing in step (I) is performed until not less than 20%, preferably not less than 50%, more preferably not less than 70%, of the cells contained in the cell aggregate become midbrain-hindbrain boundary neural progenitors. Since the culturing period may vary depending on the animal species of pluripotent stem cells; and the kind and concentration of the ROCK inhibitor, TGFβ signal inhibitor and the first fibroblast growth factor, it cannot be generally specified. However, when human pluripotent stem cells are used, for example, the first culturing step is generally for 14-30 days (e.g., 21 days).

As the midbrain-hindbrain boundary marker, En2 (midbrain marker), Gbx2 (rostral hindbrain marker) and others can be mentioned. As the neural progenitor marker, N-cadherin can be mentioned. Therefore, in one embodiment, the midbrain-hindbrain boundary neural progenitor can be identified as an En2- or Gbx2-positive, and N-cadherin-positive cell.

Step (I) may comprise a step for confirming induction of differentiation into midbrain-hindbrain boundary neural progenitor tissue in the cell aggregate. The confirmation step can be performed by separating a part of the cell aggregate, and subjecting same to RT-PCR using midbrain-hindbrain boundary marker specific probe, or immunohistochemical analysis using midbrain-hindbrain boundary marker specific antibody and neural progenitor tissue specific antibody.

In one embodiment, a sonic hedgehog inhibitor is not added to the suspension culturing in step (I), and the suspension culturing in step (I) does not contain a sonic hedgehog inhibitor throughout the whole period thereof. That is, the pluripotent stem cell aggregate or an aggregate derived therefrom is not treated with a sonic hedgehog inhibitor. In the method of Muguruma, K. et al., Nature Neurosci. 13, 1171-1180, 2010, a sonic hedgehog inhibitor is required for cerebellar differentiation from mouse ES cells, whereas effective differentiation of pluripotent stem cells (particularly human pluripotent stem cells) into midbrain-hindbrain boundary neural progenitor tissue is possible by the method of the present invention, without adding a sonic hedgehog inhibitor. Rather, addition of a sonic hedgehog inhibitor suppresses differentiation into midbrain-hindbrain boundary neural progenitor tissue. Examples of the sonic hedgehog inhibitor include, but are not limited to, low-molecular-weight compounds such as cyclopamine, jervine, GANT61, SANT-2, tomatidine, zerumbone, GDC-0449, XL139, IPI926, IPI609, LDE225, triparanol, AY9944 and others.

In one embodiment, BMP4 is not added to the suspension culturing in step (I), and the suspension culturing in step (I) is substantially free of BMP4 throughout the whole period thereof. That is, the pluripotent stem cell aggregate or an aggregate derived therefrom is not treated with BMP4. In the method of Muguruma, K. et al., Nature Neurosci. 13, 1171-1180, 2010, BMP4 is required for cerebellar differentiation from mouse ES cells, whereas differentiation of pluripotent stem cells (particularly human pluripotent stem cells) into midbrain-hindbrain boundary neural progenitor tissue is possible by the method of the present invention, without adding BMP4. Being "substantially free of BMP4" means that the concentration of BMP4 in the medium is lower than the physiological activity expressing level. Specifically, the concentration of BMP4 in the medium is generally less than 0.1 ng/ml, preferably less than 0.01 ng/ml, more preferably less than 0.001 ng/ml, most preferably 0 ng/ml.

In a preferable embodiment, sonic hedgehog inhibitor and BMP4 are not added to the suspension culturing in step (I), and the suspension culturing in step (I) is free of a sonic hedgehog inhibitor and substantially free of BMP4 throughout the whole period thereof. That is, the pluripotent stem cell aggregate or an aggregate derived therefrom is not treated with a sonic hedgehog inhibitor and BMP4.

(3.2) Step (II)

In step (II), the human cell aggregate containing midbrain-hindbrain boundary neural progenitor tissue obtained in step (I) is further subjected to suspension culturing in a serum-free medium to induce formation of a neuroepithelial structure by neural progenitors in the neural progenitor tissue, whereby the human cell aggregate containing the cerebellar plate tissue is obtained.

The medium to be used for step (II) can be prepared by using a medium used for culturing mammalian cells as a basal medium, in the same manner as in step (I). As the basal medium, the basal medium described in connection with step (I) can be mentioned. In a preferable embodiment, the medium used for step (II) is prepared from a medium, which is used for culturing human neurons, as a basal medium. As such basal medium, Neurobasal medium can be mentioned.

The medium used for step (II) is preferably a serum-free medium, to avoid contamination with chemically-undefined components.

The medium used for step (II) may contain a serum alternative. The serum alternative may, for example, be one comprising as appropriate an albumin, transferrin, fatty acids, collagen precursor, trace elements, 2-mercaptoethanol or 3'-thiolglycerol, or their equivalents and others. As such serum alternative, N2, B27, KSR and others can be mentioned. N2 is a known serum substitute composition containing insulin, transferrin, progesterone, putrescine and sodium selenite. The composition of B27 is described in J. Neurosci. Res., vol. 35, p. 567-576, 1993, Brain Res., vol. 494, p. 65-74, 1989 and others. N2, B27 can be purchased from Life Technologies and others. The amount of serum alternative added to the medium is not particularly limited as long as it can achieve induction of differentiation into cerebellar plate tissue. For example, when it is N2 supplement manufactured by Life Technologies, ⅟500-⅟10 volume relative to the whole volume of the medium is added. In a preferable embodiment, the medium used for step (II) contains N2. A serum alternative containing chemically-defined components is preferable. In addition, a serum alternative that does not contain a component isolated from an animal different from the animal species of the cell to be cultured (xenogeneic animal-derived component) (e.g., component isolated from a non-human animal when human cells are cultured) is preferable. Use of a chemically-undefined serum alternative and a serum alternative containing xenogeneic animal-derived component (e.g., KSR (Knockout serum replacement)) is not preferable.

The medium used for step (II) may contain other additive as long as an adverse influence is not exerted on the induction of differentiation of cerebellar plate tissue. Examples of the additive include, but are not limited to, insulin, iron source (e.g., transferrin etc.), minerals (e.g., sodium selenate etc.), saccharides (e.g., glucose etc.), organic acids (e.g., pyruvic acid, lactic acid etc.), serum proteins (e.g., albumin etc.), amino acids (e.g., L-glutamine etc.), reducing agent (e.g., 2-mercaptoethanol etc.), vitamins (e.g., ascorbic acid, d-biotin etc.), antibiotics (e.g., streptomycin, penicillin, gentamicin etc.), buffering agents (e.g., HEPES etc.) and others. Since long-term culturing in a medium containing L-glutamine may cause ammonia toxicity, L-alanyl-L-glutamine dipeptide may also be used instead of L-glutamine. In a preferable embodiment, the medium used for step (II) contains L-alanyl-L-glutamine dipeptide. L-alanyl-L-glutamine dipeptide is commercially available as, for example, Glutamax (manufactured by Life Technologies) and others.

To avoid contamination with a chemically-undefined component, a medium used for step (II) is preferably a medium whose components are chemically-defined.

Preferably, a medium used for step (II) does not contain a xenogeneic animal-derived component.

Other culturing conditions in step (II), such as culturing temperature, and $CO_2$ concentration, can be set as appropriate. The culturing temperature is, for example, about 30 to 40° C., preferably about 37° C. The $CO_2$ concentration is, for example, about 1 to 10%, preferably about 5%.

In the suspension culturing in step (II), suspension culturing of the cell aggregate may be performed in the presence or absence of feeder cells as long as induction of differentiation of the midbrain-hindbrain boundary neural progenitor tissue into cerebellar plate tissue is possible by the method of the present invention. To avoid contamination with undefined factors, the suspension culturing of cell aggregate is preferably performed in the absence of feeder cells.

As a vessel that can be used for suspension culturing of a cell aggregate, those recited as vessels that can be used for forming the aggregate of pluripotent stem cells in (2) above can be mentioned. In one embodiment, a vessel having a flat bottom such as petri dish is used.

The suspension culturing in step (II) is performed for a period sufficient for inducing formation of the neuroepithelial structure by the midbrain-hindbrain boundary neural progenitors. By performing step (II), a neuroepithelial structure containing GABAergic neural progenitors and cerebellar granule cell progenitors, namely, a cerebellar plate tissue, can be formed in the cell aggregate. The neuroepithelial structure may be an epithelial tubular tissue. Formation of a neuroepithelial structure containing GABAergic neural progenitors and cerebellar granule cell progenitors can be confirmed by detecting formation of a neuroepithelial structure containing GABAergic neural progenitor marker positive cells and cerebellar granule cell progenitor marker positive cells (i.e., GABAergic neural progenitor marker positive and cerebellar granule cell progenitor marker positive neuroepithelial structure) by, for example, immunohistochemistry using a specific antibody to GABAergic neural progenitor marker (e.g., Kirrel2, Ptf1a, Sox2), and a specific antibody to cerebellar granule cell progenitor marker (e.g., Atoh1, Barhl1). For example, the suspension culturing in step (II) is performed until not less than 30%, preferably not less than 50%, more preferably not less than 70%, of the neuroepithelial structure (e.g., N-cadherin positive neuroepithelial structure) contained in the cell aggregate in the culture becomes GABAergic neural progenitor marker positive and cerebellar granule cell progenitor marker positive. Since the culturing period may vary depending on the animal species of pluripotent stem cells; and culturing conditions such as medium composition, it cannot be generally specified. However, when human pluripotent stem cells are used, since formation of the neuroepithelial structure begins in about 3 days from the start of the suspension culturing in step (II), the culturing period of the suspension culturing is not less than 3 days. The culturing period in step (II) does not have the upper limit as long as the neuroepithelial structure containing GABAergic neural progenitors and cerebellar granule cell progenitors is maintained. When the culturing period is too long, the fragility of the cell aggregate increases, and the cell aggregate may collapse. Therefore, the culturing period is generally within 40 days, preferably within 32 days.

In one embodiment, the neuroepithelial structure has apical-basal polarity. The apical-basal polarity can be identified by immunohistochemical analysis using an apical marker (e.g., PKCζ) and an antibody to the basal marker. When the neuroepithelial structure is an epithelial tubular tissue, the apical side faces the lumen (apical side in).

Here, when the above-mentioned step (I) comprises further treating the aggregate of human pluripotent stem cells or a human cell aggregate derived therefrom with the second fibroblast growth factor, the cerebellar plate tissue (neuroepithelial structure) in the cell aggregate to be obtained in step (II) acquires dorsal-ventral polarity. More specifically, in each neuroepithelial structure, cells positive for a cerebellar neural progenitor marker (e.g., Kirrel2, Ptf1a, Atoh1, SKOR2) (which are expressed on the dorsal side in the neural tube in embryonic development) are localized on the outer side of the cell aggregate, and cells positive for a ventral marker (e.g., Nkx6.1, Foxa2) are localized on the opposite region across the lumen in the neuroepithelial structure. That is, a structure having polarity along the dorsal-ventral axis of the neural tube in embryonic development can be reproduced in the cell aggregate in vitro.

When a treatment with the second fibroblast growth factor is not performed in step (I), a majority of cell aggregates have a small rosette neuroepithelial structure. When a treatment with the second fibroblast growth factor is performed, formation of the neuroepithelial structure is promoted, and a majority (e.g., not less than 70%) of cell aggregates contain a larger flat-oval neuroepithelial structure.

In one embodiment, step (II) comprises treating the human cell aggregate containing midbrain-hindbrain boundary neural progenitor tissue or a human cell aggregate derived therefrom, with GDF7 in the suspension culturing. Treatment with GDF7 promotes differentiation into cerebellar granule cell progenitors (e.g., Atoh positive cells), and formation of rhombic lip.

GDF7 is a known cytokine, and the amino acid sequence thereof is also known. GDF7 to be used in the present invention is generally mammalian GDF7. As the mammal, those mentioned above can be recited. While GDF7 of any mammal may be used as long as the object of the present invention can be achieved, preferably GDF7 of a mammal of the same species as the cell to be cultured is used. For example, GDF7 of rodents (mouse, rat etc.) or primates (human etc.) is used. Examples of the representative amino acid sequence of human GDF7 include NCBI accession No. NP_878248.2 (updated Jan. 26, 2014), a partial sequence from the 322nd to 450th amino acids of said amino acid (mature human GDF7) and others.

The timing and duration of treatment of the cell aggregate with GDF7 is not particularly limited as long as differentiation into cerebellar granule cell progenitor is promoted. To effectively promote differentiation into cerebellar granule cell progenitor, GDF7 is added to the medium in step (II) preferably within 2 days from the start of the suspension culturing of the cell aggregate, more preferably within 1 day from the start of the start of the suspension culturing, further preferably from the start of the suspension culturing to treat the cell aggregate with GDF7. The treatment period with GDF7 is generally not less than 2 days, preferably not less than 7 days. The upper limit of the treatment period with GDF7 is not particularly limited as long as differentiation into cerebellar plate tissue is possible in the cell aggregate. To avoid an unpredictable adverse influence on the differentiation, it is generally within 21 days, preferably within 14 days. After lapse of the treatment period with GDF7, GDF7 is removed from the medium. The concentration of GDF7 in the medium during the treatment with GDF7 is a concentration capable of promoting differentiation into cerebellar granule cell progenitor. For example, this concentration is generally about not less than 10 ng/ml, preferably not less than 50 ng/ml, more preferably not less than 100 ng/ml. The upper limit of the GDF7 concentration is not particularly limited as long as differentiation into cerebellar granule cell progenitor is not adversely influenced. From the aspect of culturing cost, it is generally not more than 1000 ng/ml, preferably not more than 500 ng/ml, more preferably not more than 300 ng/ml. The GDF7 concentration may be varied in the period of treatment. For example, the concentration can be reduced to half in the latter half period.

In one embodiment, step (II) comprises treating the human cell aggregate containing midbrain-hindbrain boundary neural progenitor tissue or a human cell aggregate derived therefrom, with SDF1 in the suspension culturing. Treatment with SDF1 promotes formation of a neuroepithelial structure in the cerebellar plate tissue. Particularly, it is effective for the formation of continuous cerebellar plate neuroepithelium. In addition, rhombic lip continuous to the neuroepithelial structure may be formed.

SDF1 is a known chemokine also called CXCL12, and its amino acid sequence is also known. SDF1 to be used in the present invention is generally mammalian SDF1. Examples of the mammal include those mentioned above. SDF1 of any mammal may be used as long as the object of the present invention can be achieved. Preferably, SDF1 of a mammal of the same species as the cell to be cultured is used. For example, SDF1 of rodents (mouse, rat etc.) or primates (human etc.) is used. Examples of the representative amino acid sequence of human SDF1 include NCBI accession No. NP_001171605.1 (updated May 25, 2014), an amino acid sequence obtained by removing the N-terminus signal sequence (1-22) from said amino acid sequence (mature human SDF1) and others.

The timing and duration of the treatment of the cell aggregate with SDF1 are not particularly limited as long as formation of a neuroepithelial structure in the cerebellar plate tissue is promoted. Since SDF1 is a factor involved in the positioning of intracerebral cells, it is preferable to treat the cell aggregate with SDF1 at a stage when a neuroepithelial structure (cerebellar plate tissue) containing GABAergic neural progenitors and cerebellar granule cell progenitor is formed to a certain extent in the cell aggregate. From such aspects, SDF1 is added to the medium preferably at any time point in day 4-day 10, more preferably at any time point in day 6-day 8, from the start of the suspension culturing of the cell aggregate in step (II) to treat the cell aggregate with SDF1. The treatment period with SDF1 is generally not less than 2 days, preferably not less than 7 days. The upper limit of the treatment period with SDF1 is not particularly limited as long as differentiation into cerebellar plate tissue is possible in the cell aggregate. To avoid an unpredictable adverse influence on the differentiation, it is generally within 21 days, preferably within 14 days. After the lapse of the treatment period with SDF1, SDF1 is removed from the medium. The concentration of SDF1 in the medium during the treatment with SDF1 is a concentration capable of promoting formation of the neuroepithelial structure. For example, this concentration is generally not less than about 50 ng/ml, preferably not less than 100 ng/ml. The upper limit of the SDF1 concentration is not particularly limited as long as formation of neuroepithelial structure is promoted. From the aspect of culturing cost, it is generally not more than 1000 ng/ml, preferably not more than 500 ng/ml. The SDF1 concentration may be varied in the period of treatment. For example, the concentration can be reduced to half in the latter half period.

In a preferable embodiment, the cell aggregate is not stimulated with SDF1 from the start of the suspension culturing in step (II) up to the start of the treatment with SDF1. That is, the medium for the suspension culturing is preferably substantially free of SDF1 from the start of the suspension culturing in step (II) up to the start of the treatment with SDF1. Being "substantially free of SDF1" means that the concentration of SDF1 in the medium is lower than the concentration for promoting formation of the neuroepithelial structure. In one embodiment, the concentration of SDF1 in the medium during the period of from the start of the suspension culturing in step (II) to the start of the treatment with SDF1 is generally less than 1 ng/ml, preferably less than 0.1 ng/ml, more preferably less than 0.01 ng/ml.

In one embodiment, in the suspension culturing in step (I), an aggregate of pluripotent stem cells or a cell aggregate derived therefrom is treated with a second fibroblast growth factor (e.g., FGF19) and further, in the suspension culturing in step (II), the cell aggregate containing the midbrain-hindbrain boundary neural progenitor tissue or a cell aggregate derived therefrom is treated with SDF1. As mentioned above, by the treatment with the second fibroblast growth factor (e.g., FGF19) in step (I), the cerebellar plate tissue (neuroepithelial structure) in the cell aggregate obtained in step (II) acquires dorsal-ventral polarity. To be specific, in each neuroepithelial structure, cerebellar neural progenitor marker-positive cells are localized on the outer side of the cell aggregate, and ventral marker-positive cells are localized on the opposite region across the lumen in the neuroepithelial structure. By further treating such cell aggregate containing a cerebellar plate tissue (neuroepithelial structure) having dorsal-ventral polarity with SDF1, formation of continuous cerebellar plate neuroepithelium is promoted, and a continuous cerebellar neuroepithelial structure (e.g., Kirrel2 positive neuroepithelial structure) can be formed on a surface zone of the cell aggregate. The neuroepithelial structure has a polarity that the apical side (e.g., Sox2+ VZ cells, PKCζ positive cells) is located on the superficial side (surface of cell aggregate) and the basal side (e.g., Skor2+ Purkinje progenitors) is located in the deep portion. SDF1 treatment promotes lamination of the cerebellar neuroepithelial structure into three layers along the apical-basal axis, as seen in the early cerebellar development in embryo, and generates a three layer structure of ventricular zone (e.g., aPKC+, Sox2+, Ptf1a+, Kirrel2+), Purkinje cell precursor zone (e.g., Skor2+, Olig2+, GAD+, Lhx5+) and rhombic lip-derived nerve cell zone (e.g., Atoh1+, Barhl1+), from the apical to basal direction. Furthermore, it causes formation of a rhombic lip-like tissue at the edge of the continuous cerebellar neuroepithelial structure. The rhombic lip-like tissue exhibits a curled structure and contains Atoh1+ cells and Barhl1+ cells. As shown above, by combining the treatment with a second fibroblast growth factor (e.g., FGF19) in step (I) and the treatment with SDF1 in step (II), a cerebellar progenitor tissue having a higher structure can be formed.

In one embodiment, in the suspension culturing in step (I), the aggregate of pluripotent stem cells or a human cell aggregate derived therefrom is treated with a ROCK inhibitor from the start of the suspension culturing, treated with a TGFβ signal inhibitor from the start of the suspension culturing, treated with a first fibroblast growth factor from day 2-4 from the start of the suspension culturing, and treated with a second fibroblast growth factor from day 10-14 from the start of the suspension culturing, and further in the suspension culturing in step (II), the human cell aggregate containing midbrain-hindbrain boundary neural progenitors or a human cell aggregate derived therefrom is treated with SDF1 from day 4-10 from the start of the suspension culturing. The treatment period with the ROCK inhibitor is a period sufficient for suppressing cell death of pluripotent stem cells, which is induced by dispersion (e.g., for 12 hr (2 days, 4 days, or 7 days)-21 days (or 14 days)). The treatment period with the TGFβ signal inhibitor is a period sufficient for suppressing mesoderm differentiation and promoting differentiation into neuroectoderm (e.g., for 2 days (or 7 days)-21 days (or 14 days)). The treatment period with the first fibroblast growth factor treatment is a period sufficient for promoting differentiation of pluripotent stem cells into midbrain-hindbrain boundary neural progenitor tissue (e.g., for 2 days (or 5 days)-19 days (or 12 days)). The treatment period with the second fibroblast growth factor treatment is a period sufficient for conferring polarity along dorsal-ventral axis of the neural tube upon the neuroepithelial structure (e.g., for 2 days (or 4 days)-14 days (or 11 days or 7 days)). The treatment period with SDF1 is a period sufficient for promoting formation of a neuroepithelial structure in the cerebellar plate tissue (e.g., for 2 (or 7 days)-21 days (or 14 days)).

GDF7 and SDF1 to be used in the present invention are preferably isolated. The isolated GDF7 and SDF1 contained in a medium to be used for suspension culturing have been exogenously added to the medium. Therefore, in one embodiment, the present invention comprises a step of providing each of isolated GDF7/isolated SDF1. In one embodiment, the present invention comprises a step of exogenously adding each of isolated GDF7/isolated SDF1 to the medium to be used for suspension culturing in step (II).

(4) Induction of Purkinje Cell, Golgi Cell or Interneuron

Since the cell aggregate containing cerebellar plate tissue obtained by the above-mentioned production method of the present invention contains GABAergic neural progenitors, Purkinje cells, Golgi cells or interneurons can be produced by further culturing the cell aggregate under differentiation condition. To be specific, GABAergic neural progenitors are obtained from the cell aggregate containing a cerebellar plate tissue obtained by the above-mentioned production method of the present invention, and the GABAergic neural progenitors are cocultured with mammalian cerebellar granule cell progenitors, and the GABAergic neural progenitor to induce differentiation of the GABAergic neural progenitors into Purkinje cells, Golgi cells or interneurons.

GABAergic neural progenitors may be provided as a pluripotent stem cell-derived cell population containing the GABAergic neural progenitors. preferably, as isolated GABAergic neural progenitors. Isolation of GABAergic neural progenitors can be performed by FACS using an antibody to a marker specific to the GABAergic neural progenitor. As a GABAergic neural progenitor specific marker, Kirrel2 and others can be mentioned.

Since cerebellar granule cell progenitors are abundantly contained in the rhombic lip, rhombic lip-derived cells obtained by isolating rhombic lip of a non-human mammalian (e.g., mouse) embryo and dispersing same in an appropriate cell dispersion solution (e.g., trypsin-EDTA, TrypLE etc.) can be used as cerebellar granule cell progenitors.

The coculturing of GABAergic neural progenitors and cerebellar granule cell progenitors can be performed by mixing GABAergic neural progenitors and cerebellar granule cell progenitors at an appropriate ratio (e.g., GABAergic neural progenitors:cerebellar granule cell progenitors=1:5-1:20), and culturing the mixture on a culture vessel coated with an extracellular matrix such as laminin. As a medium to be used for the culturing, various media used for culturing cerebellar nerve cell can be used. It is preferable to add N2 and Tri-iodothyronine to the medium. In addition, Cytosine beta-D-arabinofuranoside (Ara-C) may be added to the medium (Tabata, T. et al., J. Neurosci. Method. 104, 45-53). For example, DMEM/Ham F-12 and others supplemented with N2 and Tri-iodothyronine can be used.

While the culturing period is not particularly limited as long as it is a sufficient period for differentiating the GABAergic neural progenitors into a Purkinje cell, a Golgi cell or interneuron, it is generally not less than 15 days.

The differentiation into Purkinje cells or interneurons can be confirmed by evaluating expression of a marker specific to Purkinje cell, Golgi cell or interneuron, cell shape, electrophysiological properties and others. The method of the present invention may comprise such confirmation steps. As a Purkinje cell-specific marker, L7/pcp2, Calbindin and others can be mentioned. As a marker of Golgi cell, Neurogranin and others can be mentioned. As a marker of interneuron, Parvalbumin and others can be mentioned.

In the process of differentiation into Purkinje cell, Purkinje cell specific marker (L7/pcp2, Calbindin)-positive cells having axon and dendrite are first generated. By further culturing the cell, maturation proceeds, the dendrite spines are formed, GluRdelta2 is expressed, and thereby giving rise to mature Purkinje cells. Mature Purkinje cells exhibits characteristic electrophysiological properties including (1) repetitive firing of spontaneous action potential, (2) hyperpolarization-activated cation channel current (Ih current), and (3) NMDA receptor-independent AMPA receptor dependent glutamate receipt.

Purkinje cells or interneurons can be obtained by isolating Purkinje cells, Golgi cells or interneurons from the coculture. The isolation can be performed by FACS, panning and others by using an antibody to a marker specific to each cell.

As for the coculturing of GABAergic neural progenitors and cerebellar granule cell progenitors, Muguruma, K. et al., Nature Neurosci. 13, 1171-1180, 2010 can be referred to.

(5) Induction of Cerebellar Granule Cell

Since the cell aggregate containing cerebellar plate tissue obtained by the above-mentioned production method of the present invention comprises cerebellar granule cell progenitors, cerebellar granule cells can be produced by further culturing said progenitors under differentiation conditions. To be specific, a cerebellar granule cell progenitors are obtained from the cell aggregate containing a cerebellar plate tissue obtained by the above-mentioned production method of the present invention, the cerebellar granule cell progenitors are cocultured with mammalian cerebellar cells to induce differentiation of cerebellar granule cell progenitors into cerebellar granule cells.

Cerebellar granule cell progenitors may be provided as a pluripotent stem cell-derived cell population containing cerebellar granule cell progenitors, or as isolated cerebellar granule cell progenitors. Isolation of cerebellar granule cell progenitors can be performed by FACS, panning, magnetic beads and others using an antibody to a marker specific to the cerebellar granule cell progenitor. As a cerebellar granule cell progenitor specific marker, Atoh1, Barhl1, Pax6 and others can be mentioned.

Cerebellar cells can be obtained by isolating a non-human mammalian (e.g., mouse) cerebellum and dispersing same with an appropriate cell dispersion solution (e.g., trypsin-EDTA, TrypLE etc.). Preferably, a neonatal (e.g., within 2 days after birth) non-human mammalian cerebellum is used.

The coculturing of cerebellar granule cell progenitors and cerebellar cells can be performed by mixing cerebellar granule cell progenitors and cerebellar cells at an appropriate ratio (e.g., cerebellar granule cell progenitors:cerebellar cells=1:5-1:40), and culturing the mixture on a culture vessel coated with an extracellular matrix such as laminin. As a medium to be used for the culturing, various media used for culturing cerebellar nerve cells can be used. It is preferable to add N2 to the medium. For example, DMEM/Ham F-12 supplemented with N2 and serum and others can be used.

While the culturing period is not particularly limited as long as it is a sufficient period for differentiation of the cerebellar granule cell progenitors into cerebellar granule cells, it is generally about 3-10 days (preferably, 5-8 days).

The differentiation into cerebellar granule cell can be confirmed by evaluating expression of a marker specific to the cerebellar granule cell, cell shape and others. The method of the present invention may comprise such confirmation step. As a cerebellar granule cell-specific marker, Barhl1, Pax6, MAP2 and others can be mentioned.

Since differentiated cerebellar granule cell exhibits a characteristic migrating pattern in which the cell migrates along a neurite, and then the migration direction of the cell turns to the direction perpendicular to the tangent line direction up to that point, a cell having an axon in such migration pattern can be identified as a cerebellar granule cell.

Cerebellar granule cells can be obtained by isolating cerebellar granule cells from the coculture. Isolation can be performed by FACS, panning and others by using an antibody to a marker specific to the cerebellar granule cell.

(6) Cell Aggregate, Isolated Cerebellar Progenitor Tissue, Cerebellar Progenitor Tissue-Constituting Cells, Cerebellum-Constituting Cells, and Use Thereof In a further aspect, a cerebellar progenitor tissue (cerebellar plate tissue etc.) can be isolated from the cell aggregate obtained by the above-mentioned production method of s15 the present invention. In addition, various cells constituting the cerebellar progenitor tissue can be isolated by dispersing the cerebellar progenitor tissue with an appropriate cell dispersion solution. The present invention provides a cell aggregate, a cerebellar progenitor tissue, and cerebellar progenitor tissue-constituting cells obtained by the above-mentioned production method of the present invention. Also, the present invention provides cerebellum-constituting cells (Purkinje cell, Golgi cell, interneuron, granule cell, deep cerebellar nuclei) obtained by the methods described in (4) and (5) above.

The cell aggregate, the cerebellar progenitor tissue, cerebellar progenitor tissue-constituting cells, and cerebellum-constituting cells, which are obtained by the present invention, can be used for transplantation therapy. For example, the cell aggregate, the cerebellar progenitor tissue, cerebellar progenitor tissue-constituting cells, or cerebellum-constituting cells, which are obtained by the method of the present invention, can be used as a therapeutic drug for diseases resulting from a disorder of cerebellum, or for complementing the corresponding damaged portion in a damaged condition of cerebellum. By transplanting the cell aggregate, the cerebellar progenitor tissue, cerebellar progenitor tissue-constituting cells, or cerebellum-constituting cells, which are obtained by the present invention, to a patient with a disease resulting from the disorder of cerebellum or a patient with a damaged condition of cerebellum, the disease resulting from the disorder of cerebellum or the damaged condition of cerebellum can be treated. Examples of the disease resulting from the disorder of cerebellum include symptomatic cerebellar cortical abiotrophy, olivopontocerebellar atrophy, Shy-Drager syndrome, spinocerebellar ataxia (SCA) (e.g., hereditary spinocerebellar ataxia, sporadic spinocerebellar ataxia (e.g., multiple system atrophy (MSA), cortical cerebellar atrophy (CCA))), Dandy-Walker syndrome and others. Medulloblastoma often observed in children frequently developed in vermis, and such medulloblastoma in cerebellum is also included in the diseases resulting from cerebellum disorder. Furthermore, examples of these damaged condition of cerebellum include cerebellectomized patients, patients after radiation on tumor in cerebellum, trauma.

In transplantation therapy, graft rejection due to the difference in the histocompatibility antigen is often problematic, which problem, however, can be solved by using pluripotent stem cells (e.g., induced pluripotent stem cells) established from somatic cells of the transplantation recipient. That is, in a preferable embodiment, pluripotent stem cells (e.g., induced pluripotent stem cells) established from the somatic cells of the recipient are used as pluripotent stem cells in the method of the present invention, and the cell aggregate, the cerebellar progenitor tissue, cerebellar progenitor tissue-constituting cells, or cerebellum-constituting cells, which are immunologically self for the recipient, are produced and transplanted to the recipient.

Furthermore, the cell aggregate, cerebellar progenitor tissue, cerebellar progenitor tissue-constituting cells, or cerebellum-constituting cells, which are obtained by the method of the present invention, can be used for screening and evaluation of drugs for treating diseases resulting from the disorder of cerebellum, or for the damaged condition of cerebellum. Particularly, since the cerebellar progenitor tissue obtained by the present invention, has a higher structure extremely similar to that of cerebellar progenitor tissue in a living body, it can be applied to screening for a therapeutic drug for diseases resulting from disorder of cerebellum, the damaged condition of cerebellum, tests for side effects and toxicity of pharmaceutical products, and the development of a new therapeutic method for diseases of cerebellum and others. For example, iPS cells are produced from a human patient with the aforementioned disease resulting from a disorder of cerebellum, particularly a hereditary disease resulting from a disorder of cerebellum and, using the iPS cells, a cell aggregate containing a cerebellar progenitor tissue is produced by the method of the present invention. The cerebellar progenitor tissue contained in the obtained cell aggregate may reproduce the disorder of cerebellum causing the disease of the patient in vitro. The cell aggregate containing the disordered cerebellar progenitor tissue, or the disordered cerebellar progenitor tissue isolated therefrom is cultivated in the presence or absence (negative control) of a test substance. Then, the level of disorder in the cell aggregate or the cerebellar progenitor tissue treated with the test substance is compared with that of the negative control. As a result, a test substance that reduced the level of the disorder can be selected as a candidate substance for a therapeutic drug for the disease resulting from the disorder. In addition, by administering a therapeutically effective amount of the selected substance to a patient who is the origin of the cell aggregate, or the cerebellar progenitor tissue, used for the screening, a disease resulting from a disorder of cerebellum in the patient may be treated, when a substance having confirmed safety as a medicament is used as a test substance. Furthermore, using a cell aggregate containing the disordered cerebellar progenitor tissue, or the disordered cerebellar progenitor tissue isolated therefrom, side effect, toxicity tests of a pharmaceutical product and the development of a new treatment method for a disease resulting from the disorder can be performed.

The present invention is explained in more detail in the following by referring to the following Examples, which are mere exemplifications and do not limit the scope of the present invention.

EXAMPLES

[Example 1] Formation of Midbrain-Hindbrain Boundary Neural Progenitor Tissue from Human Pluripotent Stem Cell (Method)

Human ES cells (KhES-1) subjected to maintenance culturing on MEF by a conventional method were used. To differentiate human ES cells by the serum-free floating culture of embryoid body-like aggregates with quick reaggregation (SFEBq method), human ES cells were enzymatically dispersed to single cells, according to the method of Nakano et al. (Cell Stem Cell, 10(6), 771-785, 2012), and reaggregated using a low-cell-adhesive V-bottom 96 well plate (SUMITOMO BAKELITE). 6,000 cells were seeded per well, and cultured in, as a differentiation medium, CDM medium [chemical synthesis medium without a growth factor (growth-factor-free Chemically Defined Medium; gfCDM; Wataya et al., Proc. Natl. Acad. Sci. USA, 105, 11796-11801, 2008) supplemented with insulin (7 μg/ml) and apo-transferrin (15 μg/ml)] under 5% $CO_2$ at 37° C.

The seeding day is taken as day 0 of differentiation culturing. 10 μM Y-27632 (ROCK inhibitor; inhibitor of cell death during dispersion: Watanabe et al., Nature Neuroscience, 8, 288-296, 2007) and 10 μM SB431542 (TGF-beta inhibitor) were added from day 0 to day 7. From day 2 to day 7 of culturing, FGF2 was added to the medium at a final concentration of 50 ng/ml. On day 7, ⅓ of the medium was exchanged with a differentiation medium free of Y-27632, SB431542 and Fgf2. On day 14 of culturing, the medium was completely substituted by a differentiation medium free of Y-27632, SB431542 and FGF2. The cell aggregates were fixed and sliced, and tissue differentiation was analyzed by the immunofluorescence method and quantitative PCR method.

(Results)

Figure 2:
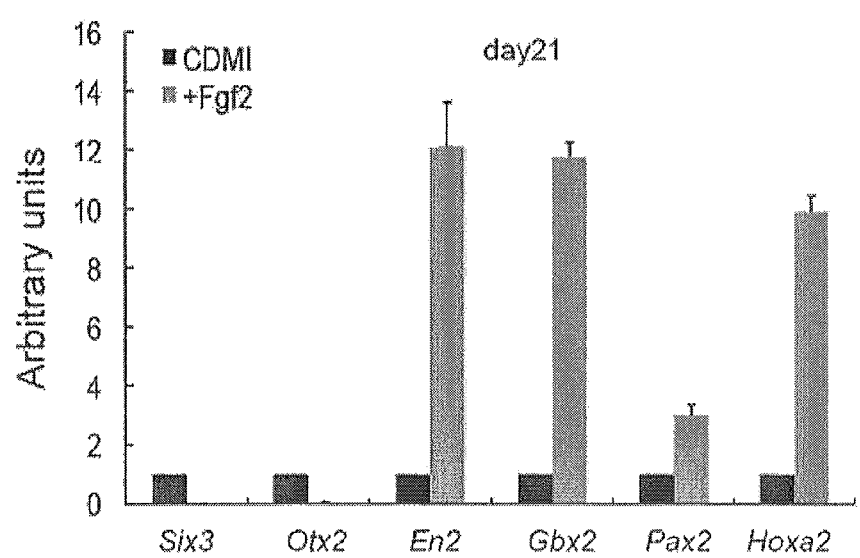
FIG. 2 shows analysis of region specific gene expression by the quantitatively PCR method. Six3 and Otx2 (forebrain); En2 (midbrain); Gbx2 (rostral hindbrain); Pax2 and Hoxa2 (caudal hindbrain). The left column (CDMI) shows Fgf2 non-addition conditions, and the right column (+Fgf2) shows Fgf2 addition conditions, respectively.

By day 14 from the start of the differentiation culturing, not less than 90% of the cells in the cell aggregate were differentiated into N-cadherin positive neural progenitors. Expression of rostral hindbrain region marker Gbx2 was observed on day 14, and not less than 80% of the N-cadherin positive cells were Gbx2 positive on day 21. At this time, expression of Otx2, which is a marker for the region rostral from the midbrain was hardly observed (FIG. 1). In addition, of the genes specific to the region along the neural tube rostrocaudal axis, the expression of midbrain-hindbrain boundary markers En2, Gbx2 was markedly increased by the addition of FGF2 (FIG. 2). An increase in the expression of En2 and Gbx2 due to FGF2 was also found on day 14 and day 21 from the start of the culturing. While FGF2 suppressed expression of forebrain markers Six3 and Otx2 (FIG. 2), it enhanced expression of Fgf8 and Wntl, which are considered to be implicated in the function of the isthmic organizer forming at the embryonic midbrain-hindbrain boundary (days 10 and 14). These results suggest that FGF2 promoted self organization of neural progenitors in the midbrain-hindbrain boundary in this method.

In the above-mentioned method, since human ES cells did not form an aggregate when Y-27632 was not added, it was suggested that the ROCK inhibitor provides effects of suppressing cell death due to dispersion, as well as supporting the cell aggregate formation and growth of pluripotent stem cells.

SB431542 induced differentiation into neural progenitors in the midbrain-hindbrain boundary at the concentration ranging of 10-30 μM. The induction of differentiation into neural progenitors was also observed at a concentration of 3 μM.

FGF2 promoted differentiation into neural progenitors in the midbrain-hindbrain boundary even at concentrations of 20 ng/ml and 100 ng/ml. FGF2 at a concentration (5-10 ng/ml) used for the maintenance culturing of ES cells did not show promotion of differentiation into neural progenitors in the midbrain-hindbrain boundary. Even when FGF2 was added to the medium from day 0 or day 1, remarkable promotion of differentiation into neural progenitors in the midbrain-hindbrain boundary was not observed. Addition of FGF2 for a period of days 2-14, days 3-7, days 4-7 each also exhibited a promoting effect on the differentiation into neural progenitors in the midbrain-hindbrain boundary, and addition of FGF2 for a period of days 2-7 showed the highest effect. When FGF8b was used instead of FGF2, differentiation into neural progenitors in the midbrain-hindbrain boundary was promoted; however, the effect was weaker than FGF2.

When medium exchange was not performed on day 7, culture of cell aggregate could be maintained up to day 14, and differentiation into neural progenitors in the midbrain-hindbrain boundary was possible; however, fragility of the cell aggregate increased and the cell aggregate became fragile.

[Example 2] Self-Formation of Cerebellar Plate Tissue Having Continuous Epithelial Structure from Human Pluripotent Stem Cells (Method)

Human pluripotent stem cell aggregates were cultured according to the method of Example 1. The was aggregates were transferred to a low-cell-adhesion 10 cm dish on and after day 21, and cultured in a neural culture medium (Neurobasal/GlutaMaxI/N2, all Life Technologies). On day 28 of culturing, the total amount of the medium was exchanged with the same neural culture medium, and differentiation of the tissue was analyzed by the immunofluorescence method on day 35 of culturing.

(Results)

Figure 3:
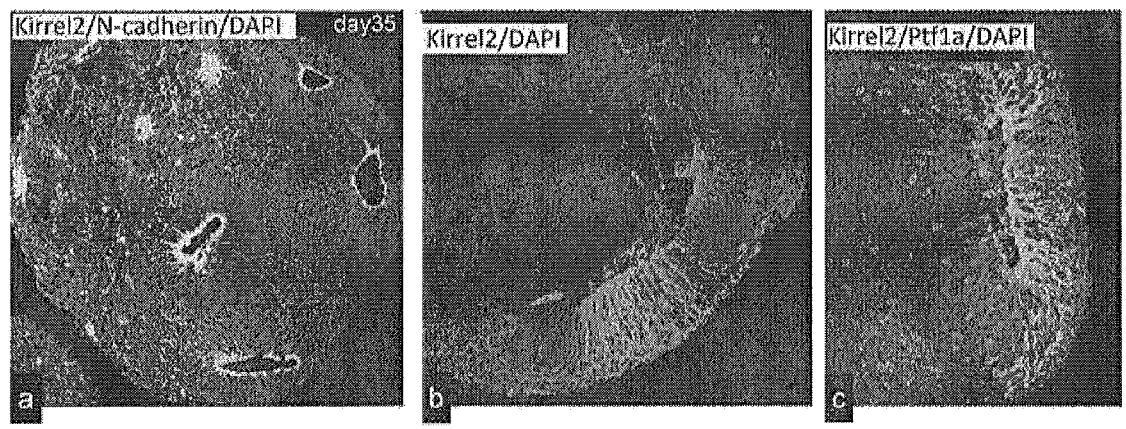
FIG. 3 shows fluorescent immunohistochemical staining images of a cell aggregate on day 35 of differentiation induction culture. a: N-cadherin (green), Kirrel2 (red). b: Kirrel2 (green). c: Kirrel2 (green), Ptf1a (red). In all images, the nuclei were counterstained by DAPI (blue).

A plurality of N-cadherin positive neuroepithelial structures were formed in one aggregate, and not less than 70% of neuroepithelial cells were positive to cerebellar GABAergic neural progenitor-specific kirrel2 (FIG. 3 left, middle). Not less than 80% of the neuroepithelial structure expressing Kirrel2 also expressed GABAergic neural progenitor-specific Ptf1a (FIG. 3, right). The Kirrel2 positive neuroepithelial structure was also En2 positive. These results clearly suggest that midbrain-hindbrain boundary region progenitors induced to differentiate by the method of Example 1 were promoted to be self-organized into cerebellar neural plate along with the formation of a neuroepithelial structure.

Even when the timing of exchange with the neural culture medium was set to day 14, day 18 and day 28, N-cadherin positive neuroepithelial structure was formed similar to that obtained when exchanged on day 21. When exchanged on day 21, a most organized neuroepithelial structure was formed.

When a hedgehog inhibitor cyclopamine (1 μM) was added on day 7-14, day 14-21, or day 21-35, differentiation into Kirrel2 positive cell was not enhanced further.

[Example 3] Differentiation of Purkinje Cell and Cerebellar Interneuron by Dispersion Culture of Human Pluripotent Stem Cell-Derived Cerebellar Plate Tissue (Method)

Human pluripotent stem cell aggregates were cultured according to the methods of Examples 1 and 2, and Kirrel2 positive cells were separated by FACS using an antibody to cerebellar GABAergic neural progenitor marker Kirrel2 on day 35 of culturing. Separated Kirrel2 positive cells, and cerebellar granule cell progenitors prepared from the upper rhombic lip of embryonic day 14 mouse were dispersed into single cells by cell dispersion enzyme (TrypLE, Life Technologies), and cocultured on a cover glass coated with poly D-lysine/laminin in DMEM/F12/10% FBS medium (5% $CO_2$, 37° C.). In coculture, human pluripotent stem cell-derived Kirrel positive cells (1 vol) relative to mouse-derived cerebellar granule cell progenitors (10 vol) were mixed. After 6-12 hr, DMEM/F12/N2/BSA/Tri-iodothyronine (T3) was added to decrease the FBS concentration to about 0.8%. Thereafter, at a frequency of once per week, a half of the medium was exchanged with DMEM/F12/N2/BSA/Tri-iodothyronine (T3)/Cytosine β-D-arabinofuranoside (Ara-C) to maintain the culture (Muguruma et al., Nature Neurosci., 13, 1171-1180, 2010). On days 15 to 115 from the start of the coculturing, cell maturation was analyzed by the immunofluorescence method.

(Results)

Figure 4:
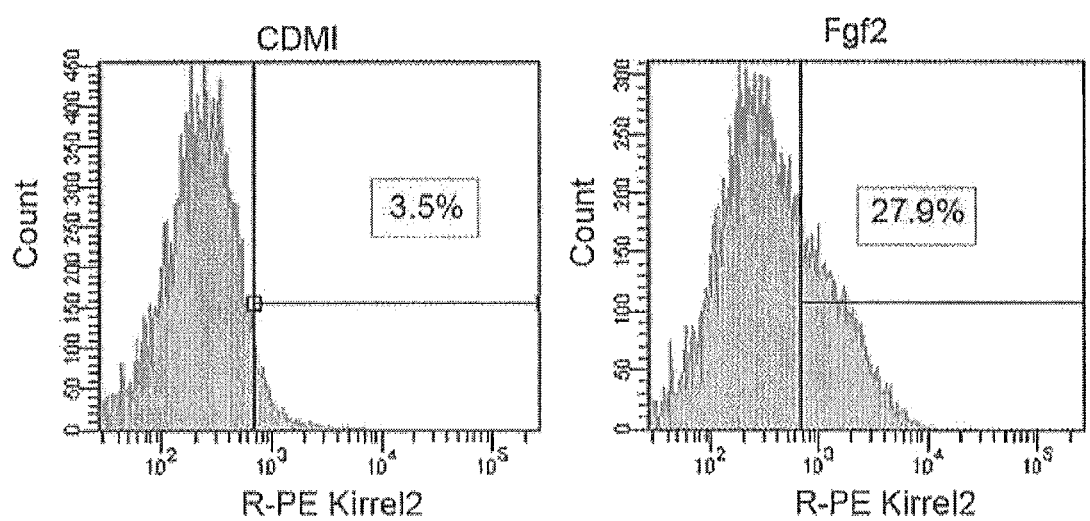
FIG. 4 shows FACS analysis by an anti-Kirrel2 antibody. left: control group, right: FGF2 addition group.

Human pluripotent stem cell aggregates were cultured according to the methods of Examples 1 and 2, and the cells were separated by FACS using an anti-kirrel2 antibody on day 35. It was observed that almost 30% of the cells exposed to Fgf2 were kirrel2 positive (FIG. 4, right).

Figure 5:
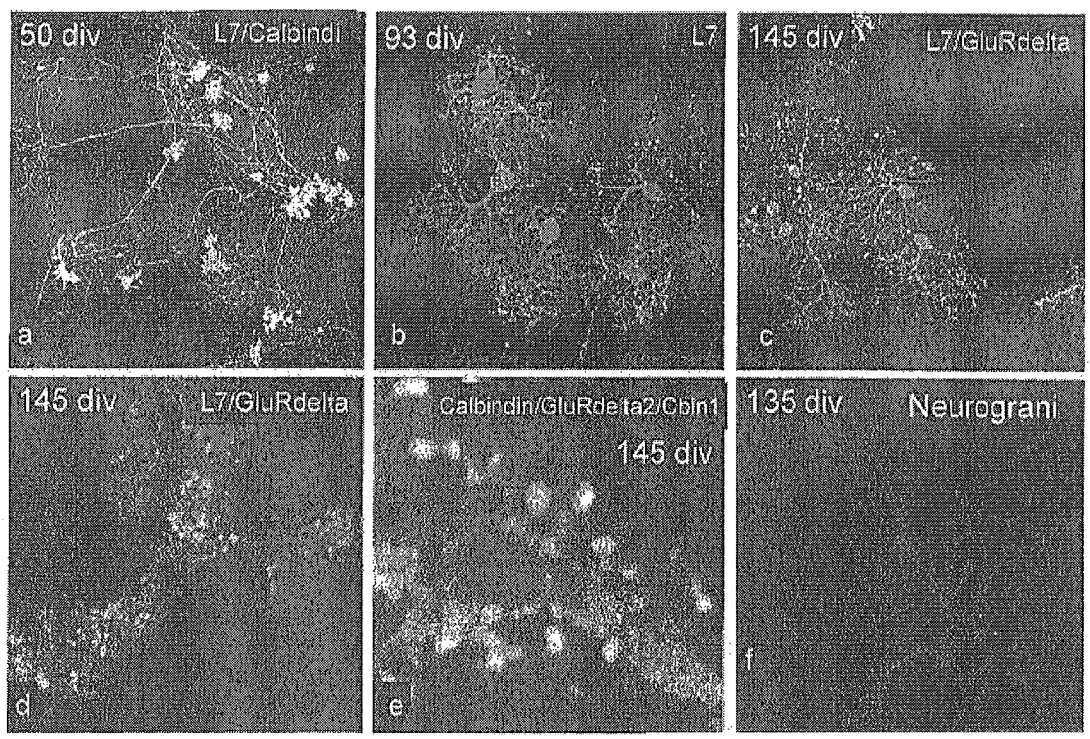
FIG. 5 shows fluorescent antibody staining images of Purkinje cells (a-e) or Golgi cells (f) obtained by coculturing the sorted Kirrel2 cells with mouse upper rhombic lip-derived cells. a: L7 (green), Calbindin (red). b: L7 (green). c: L7 (green), GluRdelta2 (red). d: L7 (green), GluRdelta2 (red). e: Calbindin (green), GluRdelta2 (white), Cblnl (red). f: Neurogranin (red).

The separated cells were cocultured with mouse upper rhombic lip-derived cells. On day 15 (after differentiation induction, total number of days 50), expression of Purkinje cell specific marker L7/pcp2 and Calbindin was observed, and extension of axons and formation of immature dendrites were observed in these marker positive cells (FIG. 5a). On day 58 of coculturing (total number of days 93), branching and extension of dendrites of L7 positive cell were observed (FIG. 5b). Emergence of such L7 positive cells was found not only in the case for human ES cells but also in the case for similarly cultured human iPS cells (4 lines). Furthermore, on day 110 of coculturing (total number of days 145), expression of Purkinje cell dendrite spine specific GluR-delta2 and morphologically clear formation of dendrite spine could be observed (FIG. 5c, d). It could be also confirmed that GluRdelta2 expressed in the dendrite spine was bonded to its ligand, CBLN1 (FIG. 5e). In this coculture system, separated kirrel2 positive cells were mostly differentiated into Purkinje cells, but some of them were differentiated into similarly kirrel2 positive GABAergic interneuron Golgi cells (FIG. 5f, neurogranin positive cell), Parvalbumin positive interneurons after long-term coculturing (58-113 days).

[Example 4] Formation of Neuroepithelial and Rhombic Lip Tissues in Human Pluripotent Stem Cell-Derived Cerebellar Plate Tissue (Method)

Human pluripotent stem cell aggregates were cultured according to the methods of Examples 1 and 2, and tissue differentiation was analyzed by the immunofluorescence method on day 35 of culturing.

(Results)

Figure 6:
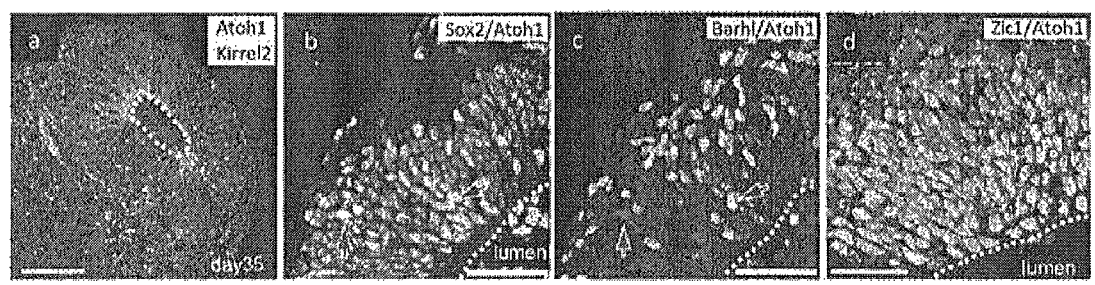
FIG. 6 shows fluorescent immunohistochemical staining images of a cell aggregate on day 35 of differentiation induction culture. a: Kirrel2 (green), Atoh1 (red). b: Sox2 (green), Atoh1 (red). c: Barhl1 (green), Atoh1 (red). d: Zic1 (green), Atoh1 (red).

On day 35 of culturing, cerebellar granule cell progenitor specific Atoh1 positive cells were observed in kirrel2 positive neuroepithelial tissue (FIG. 6a, c). Atoh1 positive cells also expressed other cerebellar granule cell markers such as Barhl1, Sox2, and Zic1 (FIG. 6b, d, e). The cerebellar nerve cells are generated from kirrel2 positive ventricular zone and Atoh1 positive rhombic lip. The results show that, according to the methods of Examples 1 and 2, differentiation of human pluripotent stem cells into kirrel2 positive ventricular zone and Atoh1 positive rhombic lip was induced, and cerebellar plate tissue was formed.

While induction of Atoh1 positive cells from the FGF2-treated mouse ES cell-derived neuroepithelial structure required addition of BMP4 (Muguruma et al., Nature Neurosci., 13, 1171-1180, 2010), Atoh1 positive cells were induced from human pluripotent stem cells without addition of BMP4.

[Example 5] Differentiation of Cerebellar Granule Cell and Cerebellar Nuclear Cell from Cerebellar Plate Tissue Derived from Human Pluripotent Stem Cells (Method)

Human pluripotent stem cell aggregates were cultured according to the methods of Examples 1 and 2, and cultured in a neural culture medium (Neurobasal/GlutaMaxI/N2) on and after day 21. The aggregates were continuously cultured by changing the total amount of the medium once per week on and after day 28 of culturing, and analyzed by the immunofluorescence method on day 35 and day 53 of culturing.

In addition, differentiation of human pluripotent stem cell-derived Atoh1 positive cells into cerebellar granule cells was analyzed by the reaggregate culture system. That is, human pluripotent stem cells were cultured according to the above-mentioned method, and dispersed into single cells on day 42-49 by using a cell dispersion reagent (TrypLE, Life Technologies). pCAG-GFP was electroporated in cells to label the cells. On the other hand, the cerebellum isolated from 2-day-old ICR system mouse was dispersed into single cells, and 20 vol thereof was mix with 1 vol of human pluripotent stem cell-derived neural progenitors labeled with GFP. The cell mixture was centrifuged to form cell aggregates, which were cultured on a cover glass coated with poly D-lysine/laminin in DMEM/F12/N2/10% FBS (5% $CO_2$, 37° C.) (Muguruma et al., Nature Neurosci., 13, 1171-1180, 2010). After reaggregate culturing, the cells were analyzed by the immunofluorescence method on day 5 and day 8.

(Results)

Figure 7:
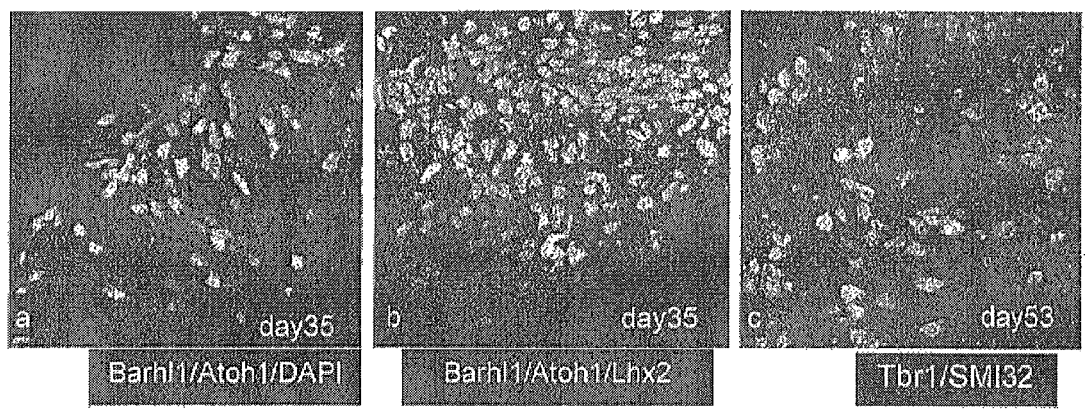
FIG. 7 shows fluorescent immunohistochemical staining images of a cell aggregate on day 35 (a and b) and day 53 (c) of differentiation induction. a: Barhl1 (green), Atoh1 (red), DAPI (blue). b: Barhl1 (green), Atoh1 (red), Lhx2 (green). c: Tbr1 (green), SMI32 (red).

Barhl1 single cells were lay laterally to Barhl1 and Atoh1 coexpressing cells in neuroepithelial tissue on day 35 of culturing, and Lhx2 positive cells were further localized on the outer side thereof (FIG. 7a, b). This indicates that Atoh1 positive rhombic lip-derived cerebellar neural progenitors migrate in the human pluripotent stem cell-derived cerebellar plate tissue, and differentiation into granule cell progenitors (Barhl1) and cerebellar nuclei progenitors (Lhx2) is progressing. Furthermore, on day 53 of culturing, large cells coexpressing rhombic lip-derived cerebellar nuclei cell progenitor markers Tbr1 and SMI32 was localized in the aggregate (FIG. 7c).

Figure 8:
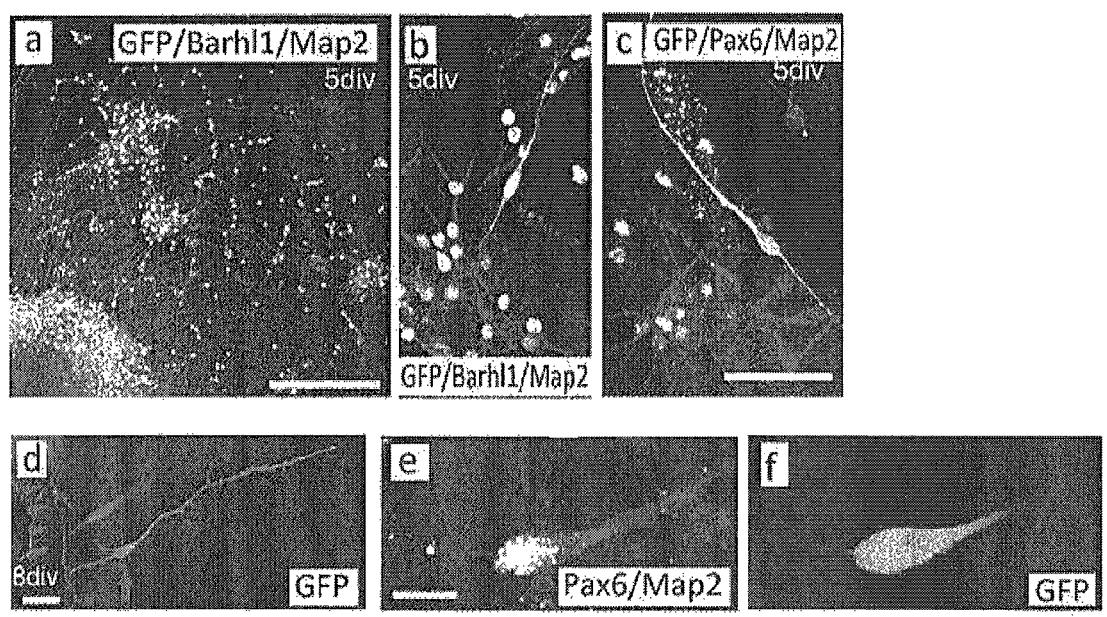
FIG. 8 shows fluorescent immunohistochemical staining images of day 5 (upper panels) and day 8 (lower panels) after reaggregation culturing. a: GFP (green), Barhl1 (white), Map2 (red). b: GFP (green), Barhl1 (white), Map2 (red). c: GFP (green), Pax6 (white), Map2 (red). d: GFP (green). e: Pax6 (white), Map2 (red). f: GFP (green).

On day 5 after reaggregate culturing, GFP-labeled human pluripotent stem cell-derived cells extended long neurites out of the cell aggregate (FIG. 8a). GFP positive cells are nerve cell specific marker MAP2 positive, and it was found that the cell soma thereof expresses cerebellar granule cell progenitor specific markers Barhl1, Pax6, and migrates along the neurite (FIG. 8b, c). On day 8, the migration direction of the cell soma turned from the tangent line direction to the perpendicular direction (FIG. 8d). It was confirmed that the cells that changed the migration direction also expressed MAP2 and Pax6. These results indicate that differentiation of human pluripotent stem cells into cerebellar granule cells could be induced, since they reproduce, in the reaggregate culture system, migration of cerebellar granule cells from the rhombic lip in the tangent line direction on the cerebellar plate surface layer, and change in the migration direction according to the development from the tangent line direction to perpendicular direction toward the cerebellar plate deeper portion.

[Example 6] Promotion of the Formation of Cerebellar Plate Tissue Having Dorsal-Ventral Axis Pattern and Periphery Tissue Thereof by Addition of FGF19

Figure 9:
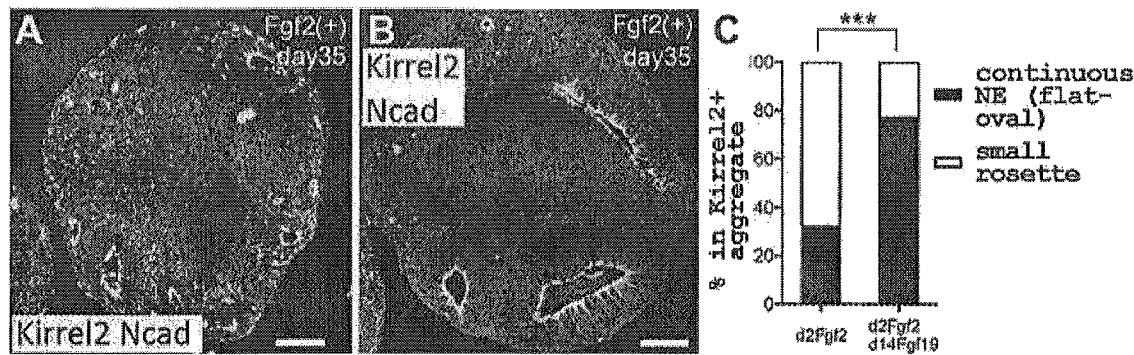
FIG. 9 shows immunohistochemical analysis of two structurally distinct Kirrel2+/N-cadherin+ neuroepithelium (NE) induced by FGF2. A: small rosette-like NE. N-cadherin (green), Kirrel2 (red). B: flat-oval continuous NE. N-cadherin (green), Kirrel2 (red). C: graph showing the ratio of cell aggregates having small rosette NE and cell aggregates having flat-oval continuous NE, when FGF19 was added.
Figure 10:
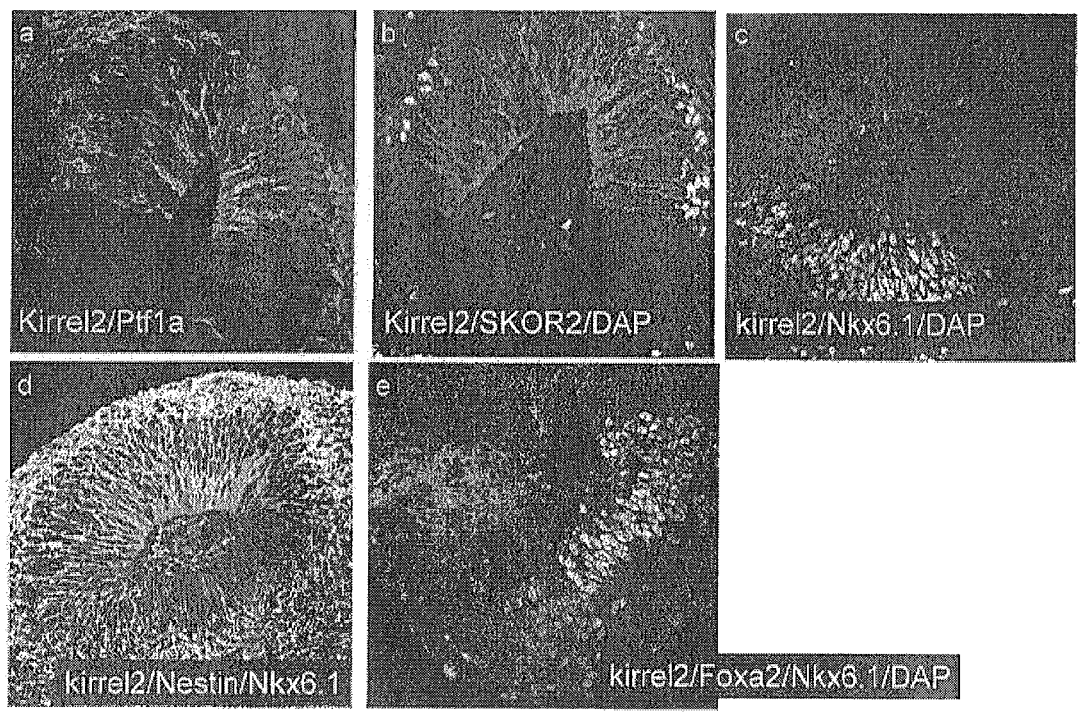
FIG. 10 shows a fluorescent antibody staining images of a cell aggregate on day 35 of differentiation induction culture. a: Kirrel2 (green), Ptf1a (red). b: Kirrel2 (green), SKOR2 (white), DAPI (blue). c: Kirrel2 (red), Nkx6.1 (white), DAPI (blue). d: Kirrel2 (green), Nestin (white), Nkx6.1 (red). e: Kirrel2 (green), Foxa2 (white), Nkx6.1 (red), DAPI (blue).
Figure 11:
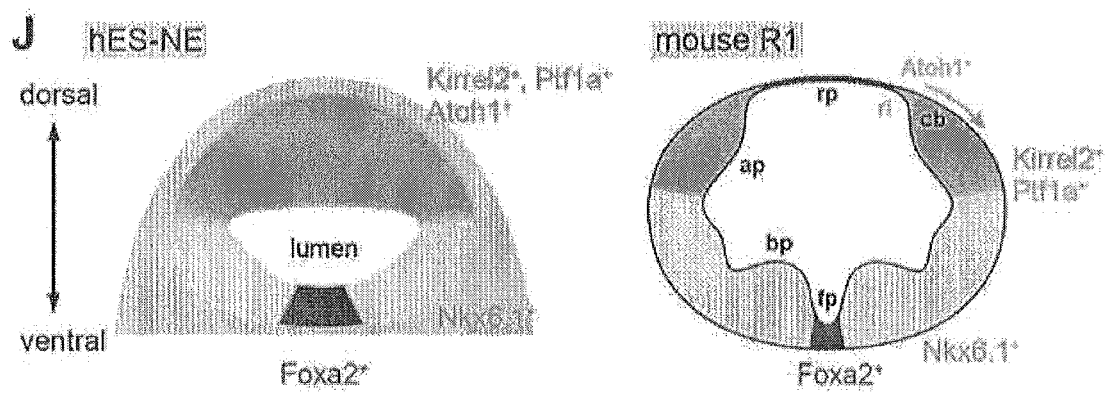
FIG. 11 is a schematic illustration showing dorsal-ventral axis of human ES cell-derived neuroepithelium and embryonic mouse rhombomere 1.

(Method)
Human pluripotent stem cell aggregates were cultured according to the methods of Examples 1 and 2. On day 14 of culturing, FGF19 was added at a final concentration of 100 ng/ml. The cells were cultured in a neural culture medium (Neurobasal/GlutaMaxI/N2) on and after day 21. On day 28, the total amount of the medium was exchanged with the same medium, and on day 35, tissue differentiation was analyzed by the immunofluorescence method.
(Results)
When FGF19 was not added, two different types of Kirrel2 positive neuroepithelial structures were observed in the cell aggregate on day 35. The majority of cell aggregates had a small rosette-like neuroepithelial structure (FIG. 9A). The rest of the cell aggregates (–30%) contained a little larger flat-oval neuroepithelial structure (FIG. 9B). The neuroepithelium in the latter type was continuous and thicker. Interestingly, Kirrel2 as a cerebellar plate neuroepithelial marker was expressed on the outer side, with reference to each cell aggregate, of a flat-oval neuroepithelial structure (FIG. 9B). Conversely, small rosette in the cell aggregate did not show localization of Kirrel2 with clear polarity (FIG. 9A).
The addition of FGF19 promoted formation of a continuous flat-oval neuroepithelial structure in the cell aggregate (FIG. 9C). The addition of FGF19 resulted in the formation of a structure having polarity along the dorsal-ventral axis of neural tube in the human pluripotent stem cell-derived neuroepithelial structures. That is, Kirrel2–, Ptf1a–, SKOR2– positive cells which are the cerebellar neural progenitor markers and expressed on the dorsal side of the neural tube are localized on the outer side with reference to the cell aggregate, and occupied ⅓-½ of the region of each neuroepithelial structure. Atoh1 was also expressed on the outer side. In contrast, ventral markers Nkx6.1, Foxa2 were expressed on the opposite region (inner side with reference to the cell aggregate) (FIG. 10). These results indicate that FGF19 promotes self-formation of a rostral hindbrain neural tube-like structure with the dorsal side superficial clear dorsal-ventral polarity, in tertiary culture of human pluripotent stem cells (FIG. 11).
While FGF19 promoted formation of a structure having polarity along the dorsal-ventral axis of the neural tube in the neuroepithelial structures even at a concentration of 50 ng/ml, the effect thereof (frequency) was about ⅓ of that at 100 ng/ml. 300 ng/ml of FGF19 similarly promoted formation of the dorsal-ventral axis pattern. The effect (frequency) thereof was of the same level as that at 100 ng/ml. Even when FGF19 was added on day 10 of culturing, formation of a dorsal-ventral axis pattern was promoted, though the efficiency was low. When FGF8 or FGF17 was used instead of FGF19, formation of a dorsal-ventral axis pattern was promoted like FGF19, though the effect was weaker than FGF19.

[Example 7] Promotion of Formation of Rhombic Lip in Cerebellar Plate Tissue by Addition of GDF7

Figure 12:
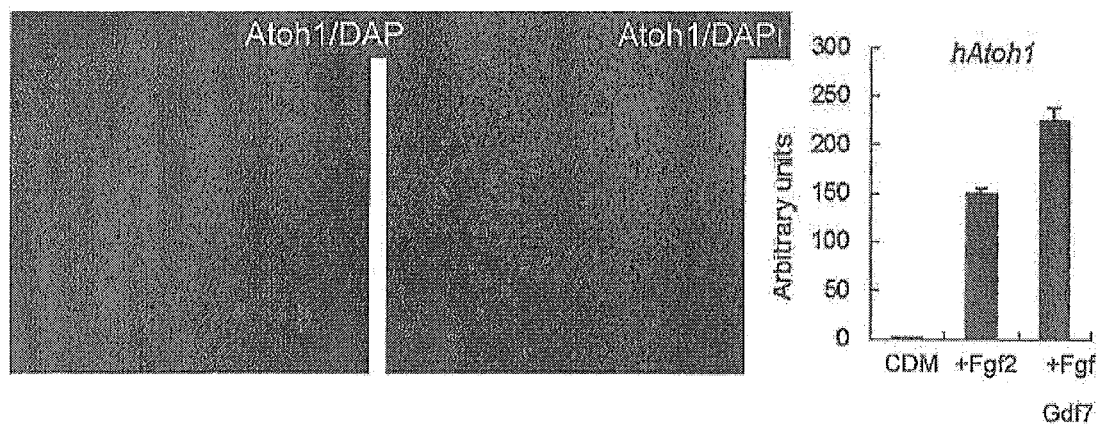
FIG. 12 shows fluorescent immunohistochemical staining images of cell aggregate on day 35 of culturing (left and center) and Atoh1 gene expression analysis by the quantitative PCR method (right). Atoh1 (red), DAPI (blue).

(Method)
Human pluripotent stem cell aggregates were cultured according to the method of Example 6. On day 21, GDF7 was added at a final concentration of 100 ng/ml. The cells were continuously cultured in a neural culture medium (Neurobasal/GlutaMaxI/N2). On day 28, the total amount of the medium was exchanged with the same medium free of GDF7, and on day 35, the cells were analyzed by the immunofluorescence method and the quantitative PCR method.
(Results)
The addition of GDF7 promoted expression of Atoh1 positive cell in human pluripotent stem cell-derived neural progenitor tissue (FIG. 12 left, center). In the gene level, it increased to about 220-fold that by the addition of FGF2, and 1.5-fold that by the addition of FGF2 (FIG. 12, right). These results indicate that the addition of GDF7 on day 21 of culturing promoted formation of the rhombic lip.
Even when GDF7 was added from day 14 of culturing, Atoh1 positive cell was induced; however, the growth of cell aggregate was inhibited, the size of the cell aggregate became small, and the neuroepithelial structure tended to collapse. On and after day 28, an adverse influence on the formation of the rhombic lip was not found even without removal of GDF7 from the medium.
In mouse, it is known that BMP4 promotes formation of rhombic lip. However, formation of the rhombic lip from human pluripotent stem cell could not be induced by using BMP4 instead of GDF7 in the above-mentioned test system. This suggests that the factors necessary for inducing rhombic lip from pluripotent stem cells in vitro are different between mouse and human, and GDF7 is important for the formation of the rhombic lip in human and GDF7 cannot be replace by BMP4.

[Example 8] Promotion of Formation of Rhombic Lip in Cerebellar Plate Tissue and Formation of 3 Layer Structure of Cerebellar Plate by the Addition of SDF1

Figure 13:
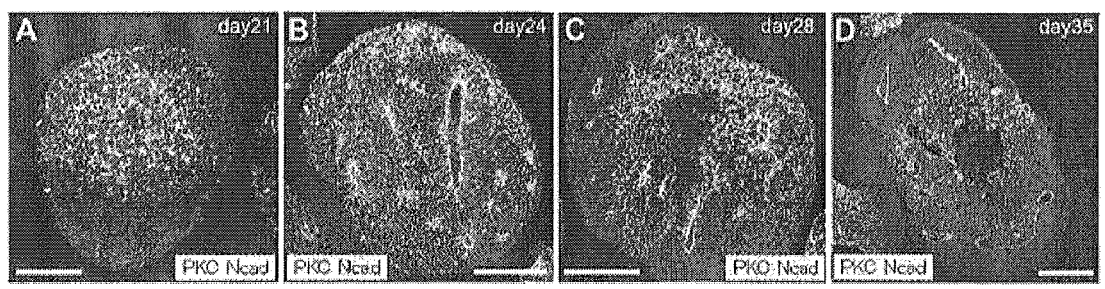
FIG. 13 shows self-formation of neuroepithelial structures in a human ES cell aggregate. PKCζ (green), N-cadherin (red).

(Method)
Human pluripotent stem cell aggregates were cultured according to the method of Example 6. On and after day 21, the cells were cultured in a neural culture medium (Neurobasal/GlutaMaxI/N2). On day 28, the total amount of the medium was exchanged with the same medium, and SDF1 was added at a final concentration of 300 ng/ml. On day 35, differentiation of the tissue was analyzed by the immunofluorescence method.
(Results)
Time-course changes (temporal aspects) in the self-formation of a large flat-oval neuroepithelium were examined under SDF1 non-addition conditions. On day 21, the neural tissue formed in the cell aggregate hardly showed epithelial formation or apical-basal polarity (FIG. 13A). Up to days 24-28, neuroepithelial structures having apical-basal polarity were formed; however, the majority was small rosette (FIG. 13B, C). By day 35, the neuroepithelial rosette was converted to a large flat-oval structure with the apical side located on the inner side (apical side in) (FIG. 13D).

Figure 14:
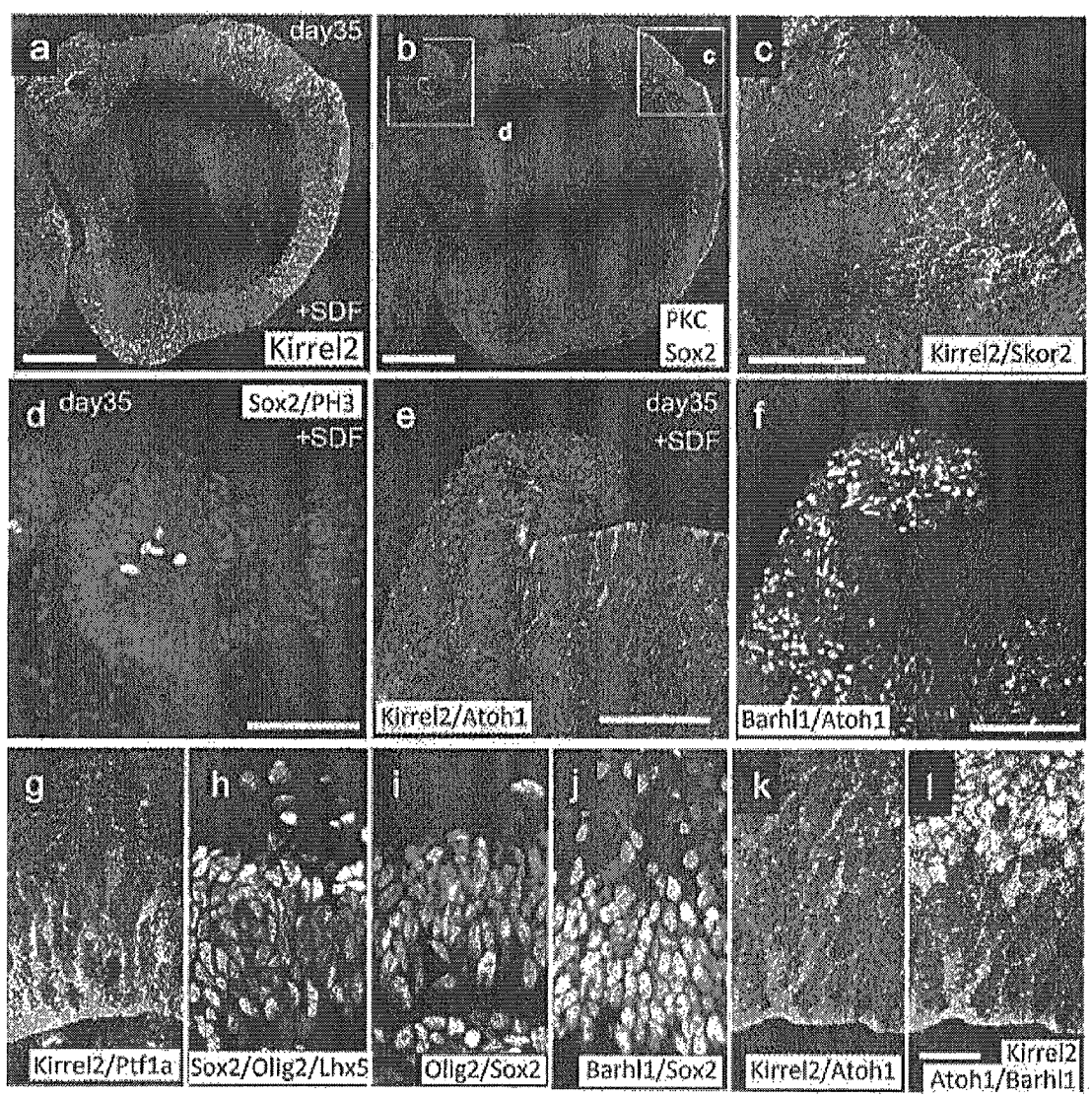
FIG. 14 shows a fluorescent antibody staining images of a cell aggregate on day 35 of culturing in a test for cerebellar tissue formation by SDF1 treatment. a: Kirrel2 (green). b: PKC (green), Sox2 (red). c: Kirrel2 (green), Skor2 (red). d: Sox2 (red), PH3 (white). e: Kirrel2 (green), Atoh1 (red). f: Barhl1 (green), Atoh1 (red). g: Kirrel2 (green), Ptf1a (red). h: Sox2 (green), Oligo2 (red), Lhx5 (white). i: Oligo2 (red), Sox2 (white). j: Barhl1 (green), Sox2 (white). k: Kirrel2 (green), Atoh1 (red). l: Kirrel2 (green), Atoh1 (red), Barhl1 (white).

The addition of SDF1 promoted formation of a continuous kirrel2 positive neuroepithelial structure (FIG. 14a-c). Different from SDF1 non-treated neuroepithelium, SDF1 treated cerebellar neuroepithelium (Kirrel2+) was continuously formed on the surface region of the cell aggregate, with the apical side placed on the outer side (apical side out) (FIGS. 14a and b; consistent with this idea, Sox2+ventricular zone cells were located on the superficial side of the neuroepithelium, and Shor2+Purkinje progenitors were located in deeper portion; FIG. 14c). At the edge of the kirrel2 positive neuroepithelium, a curled tissue containing Sox2 positive neural progenitors is formed, and Atoh1, barhl1 positive cells were localized (FIG. 14d-f). These results indicate that the addition of SDF1 promotes formation of a kirrel2 positive neuroepithelial structure from human pluripotent stem cells, and enables continuous configuration of the rhombic lip. It was further clarified that, in the continuous neuroepithelium, a 3 layer structure including ventricular zone (Kirrel2, Sox2, Ptf1a positive), Purkinje cell layer (Lhx5, Oligo2 positive), and rhombic lip derived from nerve cell layer (Atoh1, Barh1 positive) are continuously self-formed from the apical surface (FIG. 14 g-l).

SDF1 at concentrations of 100 ng/ml and 500 ng/ml also promoted formation of rhombic lip and formation of a 3 layer structure of cerebellar plate in the cerebellar plate tissue. Even when SDF1 was added from day 21, an effect similar to that when added from day 28 was observed. Matrigel or laminin could not substitute SDF1.

Figure 15:
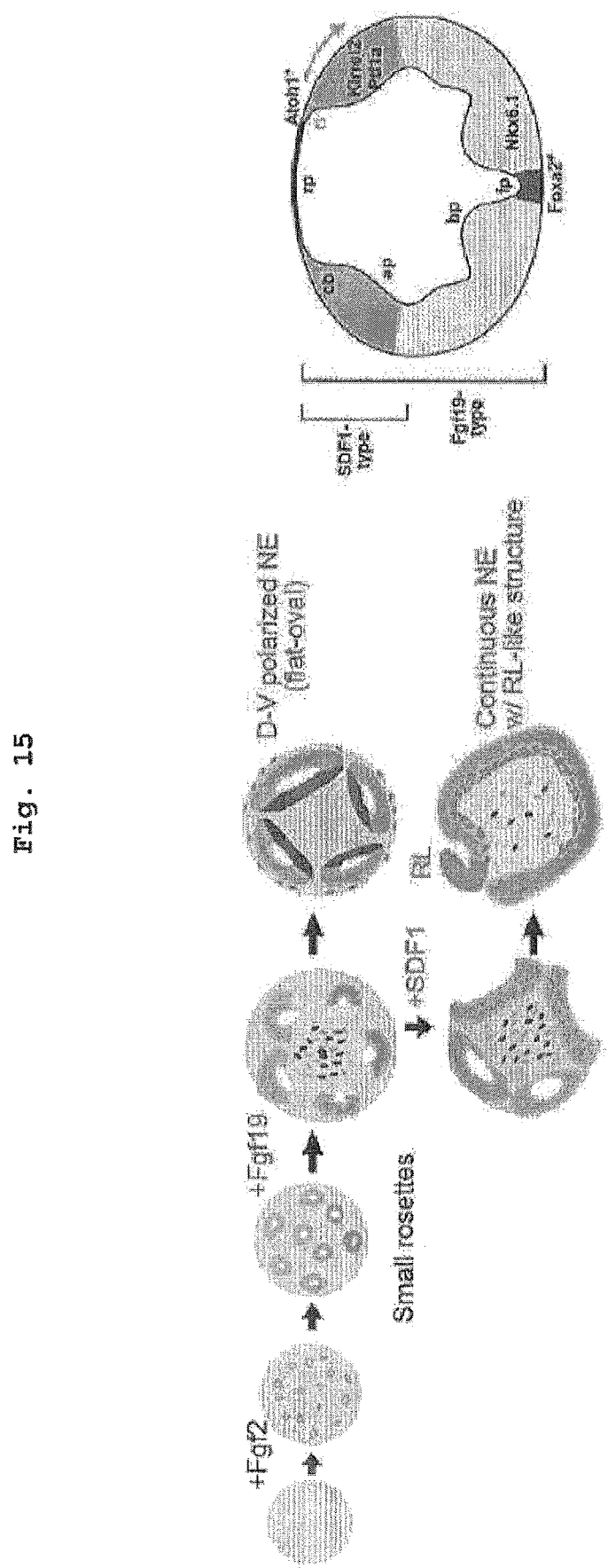
FIG. 15 is a schematic illustration showing self-formation, in two reports, of polarized cerebellar NE and continuous NE with RL-like structure induced by FGF19 and additional SDF1, respectively. SVZ: subventricular zone, VZ: ventricular zone.

From the above, it was suggested that the human pluripotent stem cell-derived aggregate treated with FGF2 and FGF19 can self-form a continuous neuroepithelium having dorsal-ventral polarity, and additional SDF1 treatment promotes spontaneous formation of an Atoh+/Barhl1+rhombic lip-like structure and a laminated cerebellar neuroepithelial structure, such as those observed in the early cerebellar development (FIG. 15).

[Example 9] Functional Analysis of Purkinje Cell Induced from Human Pluripotent Stem Cell (Method)

Mature Purkinje cells were differentiated from human pluripotent stem cell aggregates according to the method of Example 3. Using the Patch clamp technique, the electrophysiological reaction thereof was analyzed.

(Results)

Figure 16:
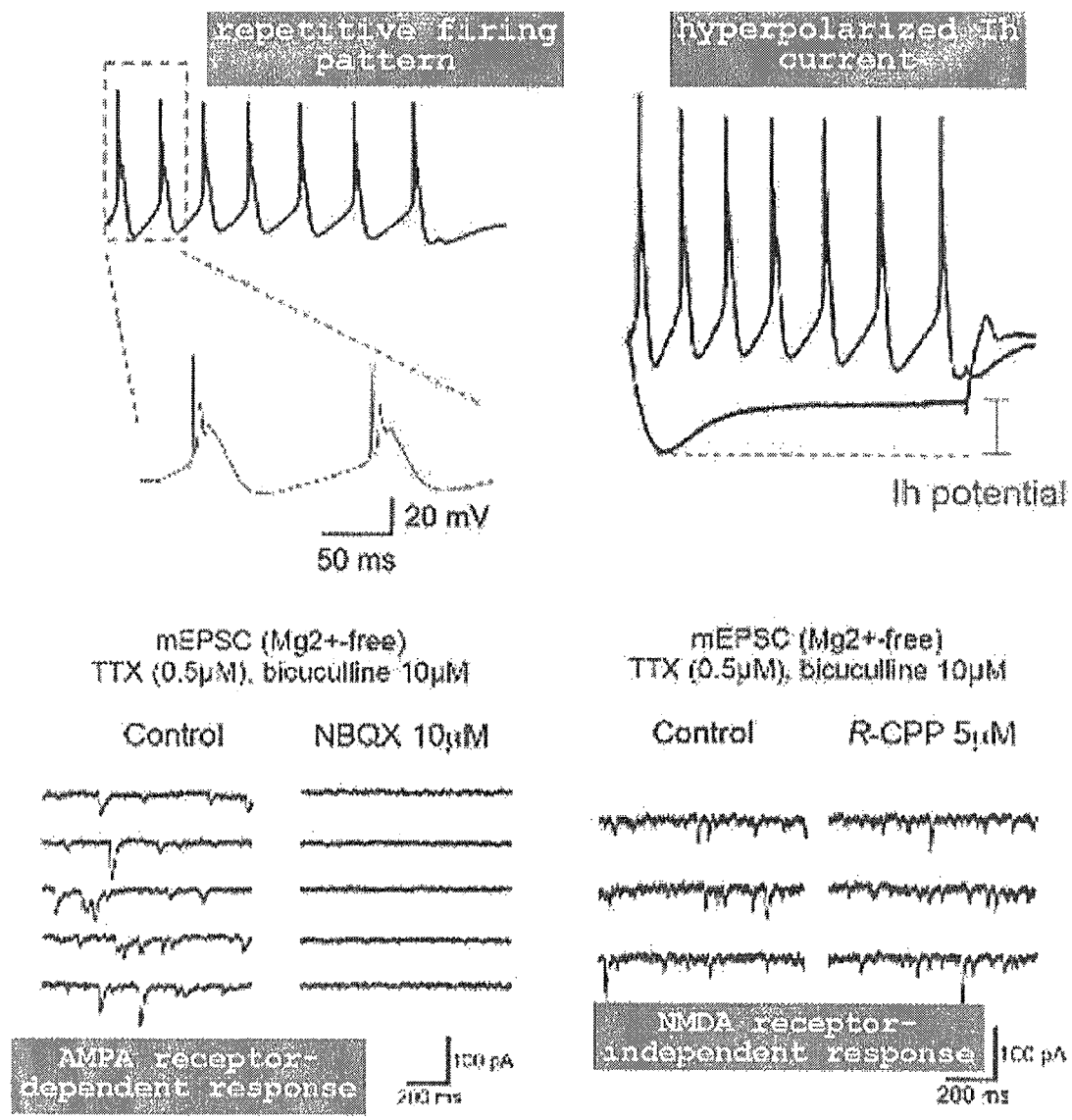
FIG. 16 shows an electrophysiological properties characteristic of Purkinje cells, which were observed in the Purkinje cells induced from a human pluripotent stem cell aggregate.

Four electrophysiological reactions characteristic of Purkinje cell could be observed (FIG. 16). The first one is repetitive firing of spontaneous action potential. The second one is a hyperpolarization-activated cation channel current (Ih current). The third one is suppression of miniature excitatory postsynaptic current by AMPA receptor inhibitor (NBQX). The fourth one is that the miniature excitatory postsynaptic current is not suppressed by NMDA receptor inhibitor. These characteristics suggest that "glutamate receipt is not mediated by NMDA receptor but depends on AMPA receptor" which is characteristic of Purkinje cell.

INDUSTRIAL APPLICABILITY

According to the present invention, cerebellar progenitor tissue can be efficiently induced from human pluripotent stem cells in vitro. The present invention is useful for the development of a therapeutic drug for diseases resulting from disorders of cerebellum, tests for side effects and toxicity, and the development of a new therapeutic method for the diseases and others.

While the present invention has been described with emphasis on preferred embodiments, it is obvious to those skilled in the art that the preferred embodiments can be modified. The present invention intends that the present invention can be embodied by methods other than those described in detail in the present specification. Therefore, the present invention encompasses all modifications encompassed in the gist and scope of the appended "CLAIMS."

The contents disclosed in any publication cited herein, including patents, patent applications and scientific literatures, are hereby incorporated in their entireties by reference, to the extent that they have been disclosed herein.

This application is based on a patent application No. 2014-182758 filed in Japan (filing date: Sep. 8, 2014), the contents of which are incorporated in full herein.

The invention claimed is:

1. A method for producing a human cell aggregate comprising a cerebellar progenitor tissue, comprising
   (I) subjecting an aggregate of human pluripotent stem cells to suspension culturing in a serum-free medium containing insulin, and treating, in the suspension culturing, the aggregate of human pluripotent stem cells or a human cell aggregate derived therefrom with a Rho-associated coiled-coil kinase (ROCK) inhibitor, a transforming growth factor β (TGFβ) signal inhibitor, and a first fibroblast growth factor, to obtain a human cell aggregate containing a midbrain-hindbrain boundary neural progenitor tissue, and
   (II) subjecting the obtained human cell aggregate containing the midbrain-hindbrain boundary neural progenitor tissue to further suspension culturing in a serum-free medium to induce formation of a neuroepithelial structure by neural progenitors in the neural progenitor tissue, thereby obtaining the human cell aggregate containing the cerebellar plate tissue;
   wherein the aggregate of human pluripotent stem cells or a human cell aggregate derived therefrom is not treated with a sonic hedgehog inhibitor in the suspension culturing of step (I).

2. The production method according to claim 1, which comprises further treating, in the suspension culturing in step (I), the aggregate of human pluripotent stem cells or the human cell aggregate derived therefrom with a second fibroblast growth factor.

3. The production method according to claim 2, wherein the second fibroblast growth factor is fibroblast growth factor (FGF) 19 (FGF19), FGF17 or FGF8.

4. The production method according to claim 2, wherein the suspension culturing in step (II) is performed until the cerebellar plate tissue acquires dorsal-ventral polarity.

5. The production method according to claim 1, which comprises treating, in the suspension culturing in step (II), the human cell aggregate containing the midbrain-hindbrain boundary neural progenitors or a human cell aggregate derived therefrom with stromal cell-derived factor 1 (SDF1).

6. The production method according to claim 5, wherein the suspension culturing in step (II) is performed until a cerebellar plate tissue comprising continuous cerebellar neuroepithelial structure and rhombic lip-like tissue on a surface layer region of the cell aggregate is formed.

7. The production method according to claim 1, which comprises treating, in the suspension culturing in step (II), the human cell aggregate containing the midbrain-hindbrain boundary neural progenitors or a human cell aggregate derived therefrom with growth differentiation factor 7 (GDF7).

8. The production method according to claim 1, wherein the aggregate of human pluripotent stem cells or a human cell aggregate derived therefrom is not treated with bone morphogenetic protein 4 (BMP4) in the suspension culturing of step (I).

9. The production method according to claim 1, wherein the first fibroblast growth factor is FGF2 or FGF8.

10. The production method according to claim 9, wherein the first fibroblast growth factor is 20 ng/ml to 100 ng/ml FGF2.

11. The production method according to claim 10, wherein the step (I) comprises culturing in the presence of 20 ng/ml to 100 ng/ml FGF2 at least from 4th to 7th day in step (I).

12. The production method according to claim 1, wherein the ROCK inhibitor is selected from a group consisting of Y-27632 ((+)-(R)-trans-4-(1-aminoethyl)-N-(4-pyridyl)cyclohexanecarboxamide), Fasudil (5-(1-homopiperazinyl)sulfonylisoquinoline), and H-1152 ((S)-(+)-2-methyl-1-[(4-methyl-5-isoquinolinyl)sulfonyl]-hexahydro-1H-1,4-diazepine), wherein the TGFβ signal inhibitor is selected from a group consisting of SB431542 (4-(5-benzol[1,3]dioxol-5-yl-4-pyridin-2-yl-1H-imidazol-2-yl)-benzamide), LY-364947, SB-505, and A-83-01, and wherein the sonic hedgehog inhibitor is selected from a group consisting of cyclopamine, jervine, GANT61, SANT-2, tomatidine, zerumbone, GDC-0449, XL139, IPI926, IPI609, LDE225, triparanol and AY9944.

* * * * *